United States Patent
St Amant, III

(10) Patent No.: US 10,866,167 B1
(45) Date of Patent: *Dec. 15, 2020

(54) WET GAS LATERAL SAMPLING SYSTEM AND METHOD

(71) Applicant: Mayeaux Holding, LLC, Gonzales, LA (US)

(72) Inventor: Valmond Joseph St Amant, III, St Amant, LA (US)

(73) Assignee: Maveaux Holdina LLC, Gonzales, LA (US)

( * ) Notice: Subject to any disclaimer, the term of this patent is extended or adjusted under 35 U.S.C. 154(b) by 222 days.

This patent is subject to a terminal disclaimer.

(21) Appl. No.: 15/977,441

(22) Filed: May 11, 2018

Related U.S. Application Data

(63) Continuation-in-part of application No. 15/615,772, filed on Jun. 6, 2017, now Pat. No. 10,436,678, and
(Continued)

(51) Int. Cl.
  *G01N 1/22* (2006.01)
  *G01N 33/22* (2006.01)

(52) U.S. Cl.
  CPC ......... *G01N 1/2247* (2013.01); *G01N 1/2205* (2013.01); *G01N 33/225* (2013.01);
  (Continued)

(58) Field of Classification Search
  CPC .. G01N 1/2247; G01N 1/2205; G01N 33/225; G01N 2001/2267; G01N 2001/2285
  See application file for complete search history.

(56) References Cited

U.S. PATENT DOCUMENTS 2,515,835 A    7/1950   Preston
3,080,760 A *   3/1963   Dirk .................. G01N 1/12
                                        73/863.31
(Continued)

FOREIGN PATENT DOCUMENTS

CN          201043965       4/2008

OTHER PUBLICATIONS

ABB, Inc, Totalflow NGC8206 Chromatograph User's Manual, (Copyright 2009, Ver 21015-002-rev.AE, US, See pp. 1-17, 2-25 & 2-58 through 2-64.
(Continued)

*Primary Examiner* — Natalie Huls
(74) *Attorney, Agent, or Firm* — Joseph T Regard, Ltd pic

(57) ABSTRACT

A system for on-stream sampling of pressurized process gas such as natural gas or the like, said system optimized for use with pressurized process gas having liquid entrained therein, or otherwise referenced as "wet". In the preferred embodiment, a probe and method of sampling is contemplated to provide linear sample of fluids from a predetermined area of said fluid stream. Further taught is the method of preventing compositional disassociation of a gas sample having entrained liquid utilizing a probe having a passage formed to facilitate capillary action in fluid(s) passing therethrough. The present invention further contemplates the use of a screen or membrane provided exterior the probe tip body to block or lessen the likelihood of undesirable particulates or liquids from entering the probe.

5 Claims, 16 Drawing Sheets

Related U.S. Application Data a continuation-in-part of application No. 15/615,786, filed on Jun. 6, 2017, now abandoned, and a continuation-in-part of application No. 14/214,225, filed on Mar. 14, 2014, now Pat. No. 9,995,659.

(60) Provisional application No. 61/798,287, filed on Mar. 15, 2013.

(52) U.S. Cl.
CPC ............... *G01N 2001/2267* (2013.01); *G01N 2001/2285* (2013.01)

(56) References Cited

U.S. PATENT DOCUMENTS

| | | | |
|---|---|---|---|
| 3,133,444 A | 5/1964 | Errnst Karwat | |
| 3,866,475 A * | 2/1975 | Thompson | G01N 1/2247 73/863.03 |
| 4,086,922 A | 5/1978 | Henderson | |
| 4,091,835 A * | 5/1978 | Frampton | G05D 7/012 137/499 |
| 4,100,806 A | 7/1978 | Barbonelle | |
| 4,283,947 A | 8/1981 | George | |
| 4,301,679 A | 11/1981 | Boyle | |
| 4,312,121 A | 1/1982 | Tweed | |
| 4,442,720 A * | 4/1984 | Apley | G01N 1/2035 73/863.31 |
| 4,537,071 A * | 8/1985 | Waterman | G01N 17/00 73/866.5 |
| 4,562,749 A * | 1/1986 | Clark | G01N 1/2035 73/863.84 |
| 4,566,342 A * | 1/1986 | Kurz | G01N 1/2035 73/863.03 |
| 4,625,570 A * | 12/1986 | Witherspoon | G01N 1/20 73/863.81 |
| 4,688,537 A | 8/1987 | Calkins et al. | |
| 4,790,198 A * | 12/1988 | Awtry | G01N 1/08 73/864.64 |
| 4,791,957 A | 12/1988 | Ross | |
| 4,993,842 A | 2/1991 | Morimoto | |
| 5,109,709 A | 5/1992 | Nimberger | |
| 5,154,087 A * | 10/1992 | Wenshau | G01N 1/08 73/863.81 |
| 5,179,859 A * | 1/1993 | Van Niekerk | G01N 1/08 73/864.64 |
| 5,237,878 A * | 8/1993 | Hackenberg | G01N 1/14 73/861.34 |
| 5,440,941 A * | 8/1995 | Kalidindi | G01N 1/08 73/864.64 |
| 5,476,586 A | 12/1995 | Mayeaux | |
| 5,501,080 A | 3/1996 | McManus et al. | |
| 5,521,130 A | 7/1996 | Welker | |
| 5,531,130 A | 7/1996 | Welker | |
| 5,538,344 A | 7/1996 | Dybdahl | |
| 5,637,809 A | 6/1997 | Traina | |
| 5,746,586 A | 5/1998 | Fukuhara et al. | |
| 5,834,657 A * | 11/1998 | Clawson | G01N 1/2035 73/863.81 |
| 5,894,080 A * | 4/1999 | Dybdahl | E21B 49/086 73/1.25 |
| 6,325,843 B1 | 12/2001 | Hickox | |
| 6,357,304 B1 | 3/2002 | Mayeaux | |
| 6,605,475 B1 | 8/2003 | Taylor | |
| 6,701,794 B2 * | 3/2004 | Mayeaux | G01N 1/2035 73/863.12 |
| 6,857,328 B1 * | 2/2005 | Spurgeon | G01N 1/2202 73/863.21 |
| 6,869,800 B2 * | 3/2005 | Torgerson | B01J 8/0035 422/62 |
| 6,904,816 B2 | 6/2005 | Mayeaux | |
| 7,004,041 B2 | 2/2006 | Mayeaux | |
| 7,134,318 B2 | 11/2006 | Mayeaux | |
| 7,162,933 B2 | 1/2007 | Thompson et al. | |
| 7,471,882 B2 | 12/2008 | Peebles et al. | |
| 7,555,964 B2 * | 7/2009 | Mayeaux | G01N 1/2035 210/321.75 |
| 7,717,000 B2 * | 5/2010 | Xie | B01F 5/0682 73/863.03 |
| 7,942,065 B2 * | 5/2011 | Xie | G01F 15/02 73/861.04 |
| 7,958,794 B2 * | 6/2011 | Sahibzada | G01N 1/2247 73/23.2 |
| 8,196,480 B1 | 6/2012 | Mayeaux | |
| D674,052 S | 1/2013 | Thompson | |
| 8,522,630 B1 * | 9/2013 | Mayeaux | G01N 1/00 73/86 |
| 9,200,986 B1 * | 12/2015 | Mayeaux | G01N 1/10 |
| 9,257,027 B2 * | 2/2016 | Williamson | G08B 17/10 |
| 9,395,280 B2 | 7/2016 | Thompson et al. | |
| 9,459,185 B2 | 10/2016 | Thompson et al. | |
| 9,535,427 B2 | 1/2017 | Patterson et al. | |
| 9,995,659 B1 * | 6/2018 | St Amant, III | G01N 1/2247 |
| 10,436,678 B1 * | 10/2019 | St Amant, III | G01N 1/44 |
| 2002/0166365 A1 * | 11/2002 | Kogure | G01N 15/0255 73/28.01 |
| 2005/0087028 A1 * | 4/2005 | Widmer | G01N 1/26 73/863.03 |
| 2005/0223829 A1 * | 10/2005 | Mayeaux | G01N 17/046 73/866.5 |
| 2006/0229528 A1 | 10/2006 | Heske | |
| 2007/0158469 A1 | 7/2007 | Burgener | |
| 2007/0164562 A1 | 7/2007 | Valaskovic | |
| 2007/0217960 A1 | 9/2007 | Sekela | |
| 2008/0156073 A1 * | 7/2008 | Burns | G01N 15/0205 73/23.35 |
| 2009/0078442 A1 | 3/2009 | Lin | |
| 2010/0037770 A1 * | 2/2010 | Baldwin | B01D 45/04 95/267 |
| 2010/0145634 A1 * | 6/2010 | Pinguet | G01N 33/2823 702/45 |
| 2010/0212757 A1 | 8/2010 | Patterson et al. | |
| 2010/0319468 A1 * | 12/2010 | Peebles | G01N 1/2247 73/863.12 |
| 2011/0036445 A1 * | 2/2011 | Hall | G01N 1/2273 138/96 R |
| 2012/0033219 A1 * | 2/2012 | Hokamura | G01N 21/15 356/438 |
| 2012/0186366 A1 * | 7/2012 | Lentz | G01N 1/2214 73/863.21 |
| 2013/0052083 A1 | 2/2013 | Kirby | |
| 2013/0220036 A1 * | 8/2013 | Faust | G01N 1/02 73/863.41 |
| 2014/0000384 A1 * | 1/2014 | Reynolds | B63J 4/002 73/861.65 |
| 2014/0041463 A1 | 2/2014 | Vethe | |
| 2017/0315026 A1 * | 11/2017 | Andreussi | G01F 1/40 |

OTHER PUBLICATIONS

ACME Cryogenics, ACME Model CV Cryogenic Valve Brochure, date 2013, US, p. 2.

Federal Register, vol. 81, No. 222 BLM 43 CFR Parts 3175.111-112 "Onshore Oil and Gas Operations; Federal and Indian Oil and Gas . . . " Nov. 17, 2016, pp. 81578-81580 US.

ACME Cryogenics, Vacuum Insulated Pipe Brochure, date 2015, US.

ABB Inc, Portable NGC8206 Natural Gas Chromatograph DS_2101179, Copyright 2017, US.

Cryofab CFCL Series Vacuum Insulated Flexible Hose Product Sheet, date 2015, US.

A+ Corp LLC, Genie tm High Velocity Probe Product Sheet, PPS-SGP-HV-120803, Copyright 2003, US.

Intertec, SL Blocktherm Self-Limiting Block Heater Product Sheet, HD-662ca, date 2013, US.

Valtronics Inc, Mustang Sampling Sample Conditioning System MSCS P53, MSB-P53 vol. 1.2, (C) 2009, US.

Valtronics Inc, Mustang Sampling Pony Heated Probe Enclosure, MSB-PONYCS vol. 2.1, (C) 2009, US.

(56) References Cited

OTHER PUBLICATIONS

Welker Inc, Sample Conditioning Heated System Manual, Model SCHS, Manual IOM-132, Rev C, Apr. 20, 2016, p. 6.
Intertec, Diabox 87 Product Sheet, KD222-12en Diabox 87, date 2016.
Mustang Sampling, LLC, MSCS Product Brochure, MSB-MSCS vol. 1.4, (C) 2009-2017, US.
Mustang Sampling, LLC, Solar Powered Sample Conditioning System SPSCS Product Brochure MSB-PonySOL vol. 2.1, (C) 2014-2017, US.
Mustang Sampling, LLC, Sample Conditioning System P53 Product Brochure MSBC-P53-CE vol. 2.2 (C) 2009-2017, US.
Mustang Sampling, LLC, PONY Heated Probe Enclosure Product Brochure MSBC-C-PONYCS vol. 4.4 (C) 2009-2017, US.
A+ Corp, LLC GENIE (tm) Heated Regulator GHR Product Sheet, SCC-GHR-PS_0906 (C) 2006, US.
A+ Corp, Genie (tm) GHR Heated Regulator Product Sheet, SCC-GHROPS_1116, (C) 2012, US.
A+ Corp, LLC, GENIE (tm) GPHV General Purpose Probe product sheet, SCC-GPHV-PS_0116 (C) 2012, US.
A+ Corp, LLC, GENIE (tm) Vaporizer Product Sheet, SCC-GV-PS_0106, C 2006, US.
A+ Corp LLC, Genie (tm) 760 Direct Drive Probe Product Sheet, SCC-7600PS_0116, A+ Corp LLC, Gonzales, LA, (C) 2012, US.
US Dept Interior, BOL Operator Letter (redacted), Jan. 19, 2017 regarding FMP's (Facility Measurement Points), Jan. 19, 2017, US.
Thermon Manufacturing Co Brochure Form PAF0027-0714 "Installing Non-Heated Wires Within a Tube Bundle", Thermon Manufacturing Co, 2014, US.
Mustang Sampling LLC, Mustang Intelligent Vaporizer Sampling System Model 2 Product Sheet, Mustang Sampling, LLC, Ravenswood WV, (C) 2009-2016, US.
Welker Inc, SCHS Sample Conditioning Heated System, Product Sheet, Welker, Inc, Sugar Land, TX, (C) 2016, US.
McMaster-Carr Supply Co, Web catalog at https://www.mcmaster.com/#catalog/123/1/=1ap8126, Stainless Steel Tubing, p. 153, 2016, US.
Research Gate discussion regarding capillary in Gas Chromatograph, Printed Dec. 15, 2017, https://www.researchgate.net/post/What_is_a_capillary_column_for_GC_and_how_does_it_work.
A+Corporation LLC, Genie tm High Velocity Probe product sheet, 2003.
Matheson Gas, "The BTU Accuracy Connection to Profitability . . . " 2 page brochure, 2010.
SKC LTD, Printed May 10, 2018, "PTFE (Polytetrafluroroethylene) Membrane Filters", www.skcltd.com/uncategorized-articles/214-ptfe-polytetrafluoroethylene-filters.
A+ Corporation LLC, Genie 225 Membrane Separator Product Sheet, 2 pages, 2012.
A+ Corporation LLC, Genie 120 Membrane Separator Product Sheet, 2 Pages, 2012.
United States Patent Office, "Non-Final Rejection" in Utility U.S. Appl. No. 16/179,674, St Amant III, Inventor, dated Sep. 11, 2019, 9 Pages.
United States Patent Office, "Non-Final Rejection" in Utility U.S. Appl. No. 116/128305, St Amant III, Inventor, dated Aug. 8, 2019, 8 Pages.
United States Patent Office, "Final Rejection" in Utility U.S. Appl. No. 15/653,083, St Amant III, Inventor, dated Jul. 16, 2019, 9 Pages.
United States Patent Office, Interview Summary in Utility U.S. Appl. No. 15/653,083, St Amant III, Inventor, dated Aug. 21, 2019, 2 Pages.
United States Patent Office, "Non-Final Rejection" in U.S. Appl. No. 14/214,225 (now U.S. Pat. No. 9,995,659), St Amant, III inventor, dated Jun. 5, 2017, 11 pages.
United States Patent Office, "Final Rejection" in U.S. Appl. No. 14/214,225 (now U.S. Pat. No. 9,995,659), St Amant, III inventor, dated Nov. 10, 2016, 11 pages.
United States Patent Office, "Non-Final Rejection" in U.S. Appl. No. 15/615,772, St Amant, III inventor, dated Jan. 24, 2019, 13 pages.
United States Patent Office, "Non-Final Rejection" in U.S. Appl. No. 15/653,083, St Amant, III inventor, dated Apr. 8, 2019, 29 pages.
United States Patent Office, "Non-Final Rejection", U.S. Appl. No. 15/615,786, St Amant III, Inventor, dated Sep. 23, 2019, 12 Pages.
United States Patent Office, Office Action in Utility U.S. Appl. No. 15/979,146, St Amant III, Inventor, dated May 4, 2020, 14 Pages.
United States Patent Office, Utility U.S. Appl. No. 16/549,305, St Amant, III, Inventor, filed Aug. 23, 2019, 58 Pages (Written Specification and Figures).

\* cited by examiner

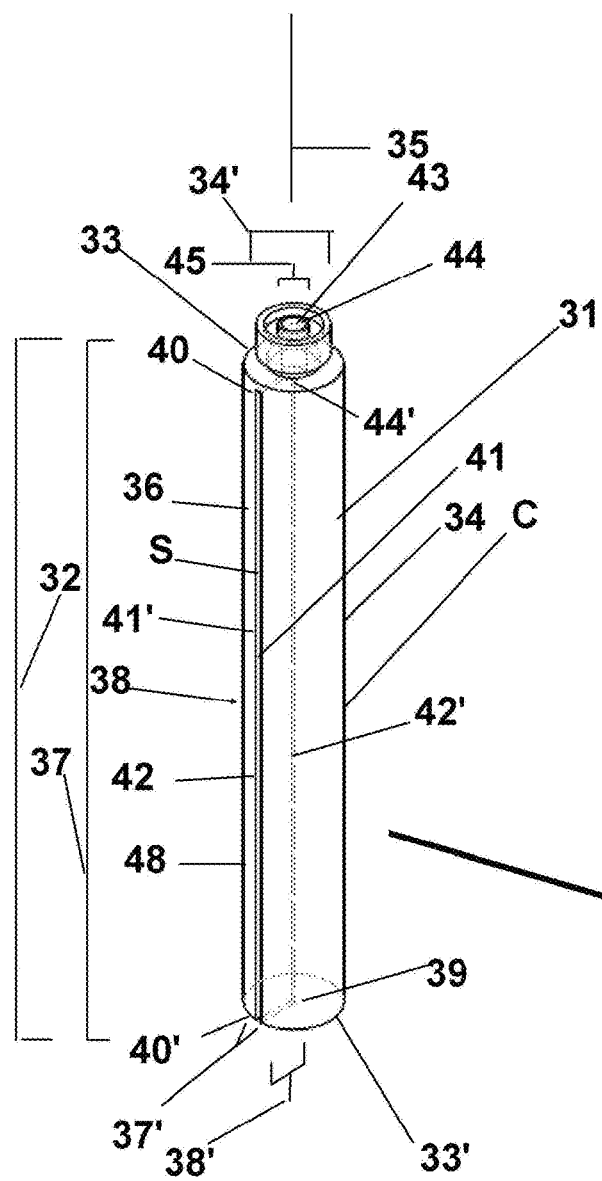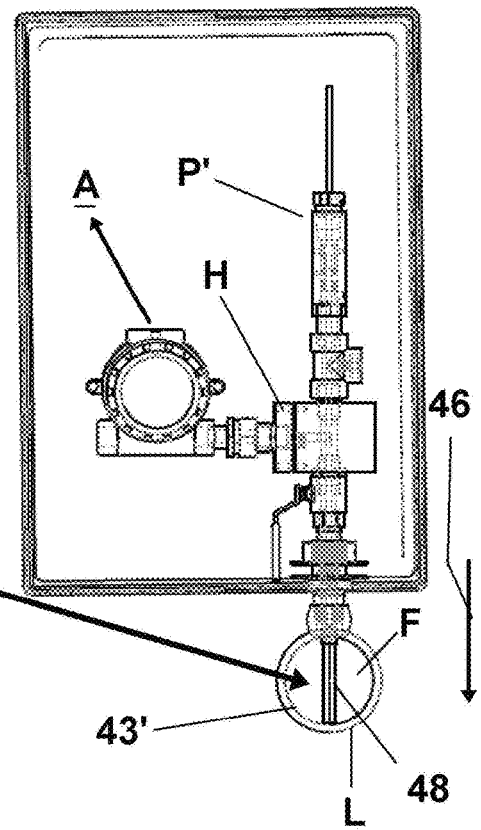
FIG 1A
FIG 1B

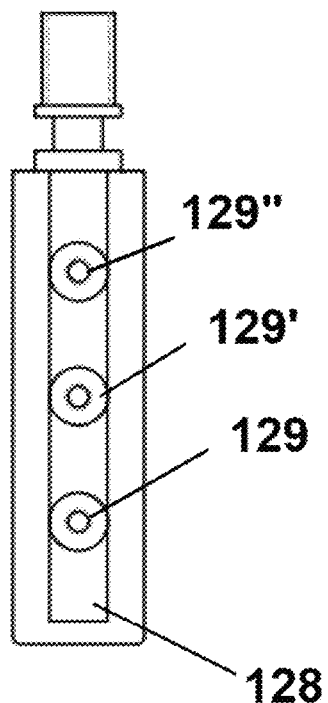
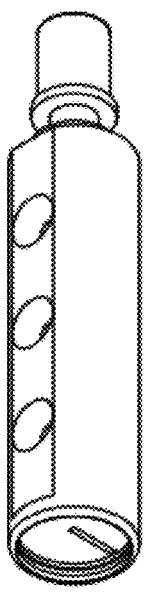
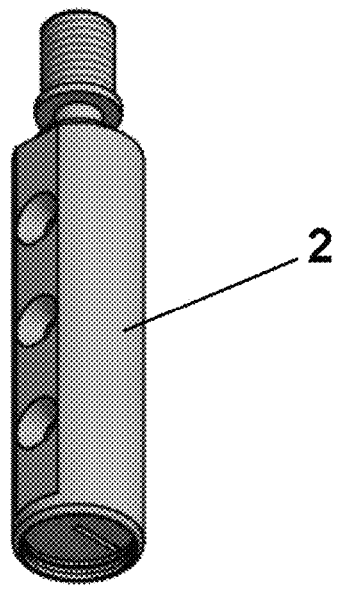
FIG 8A FIG 8B FIG 8C
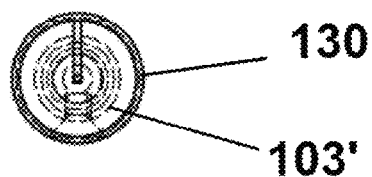
FIG 8D

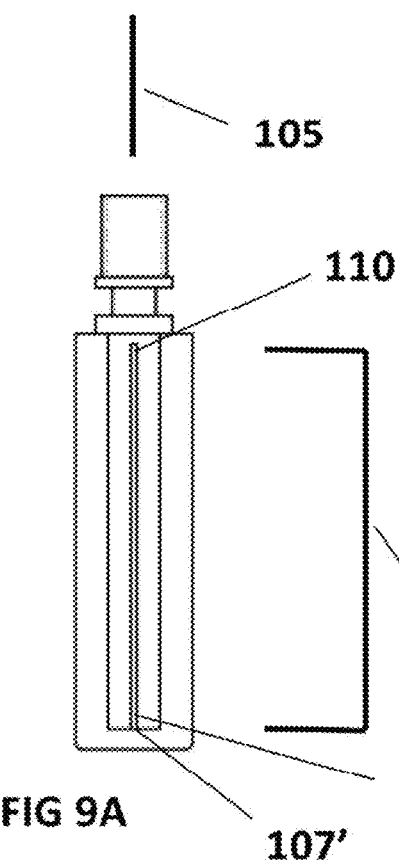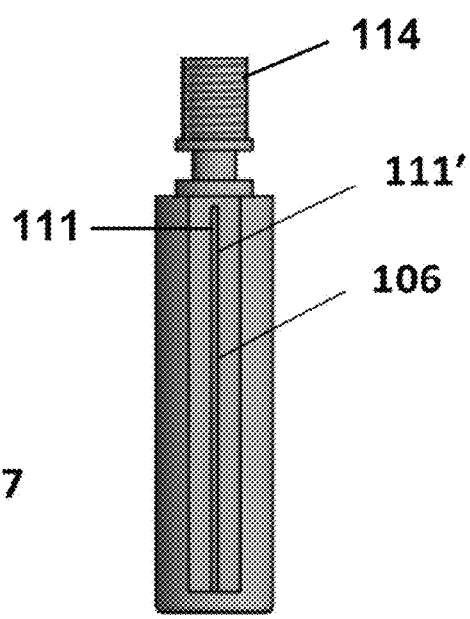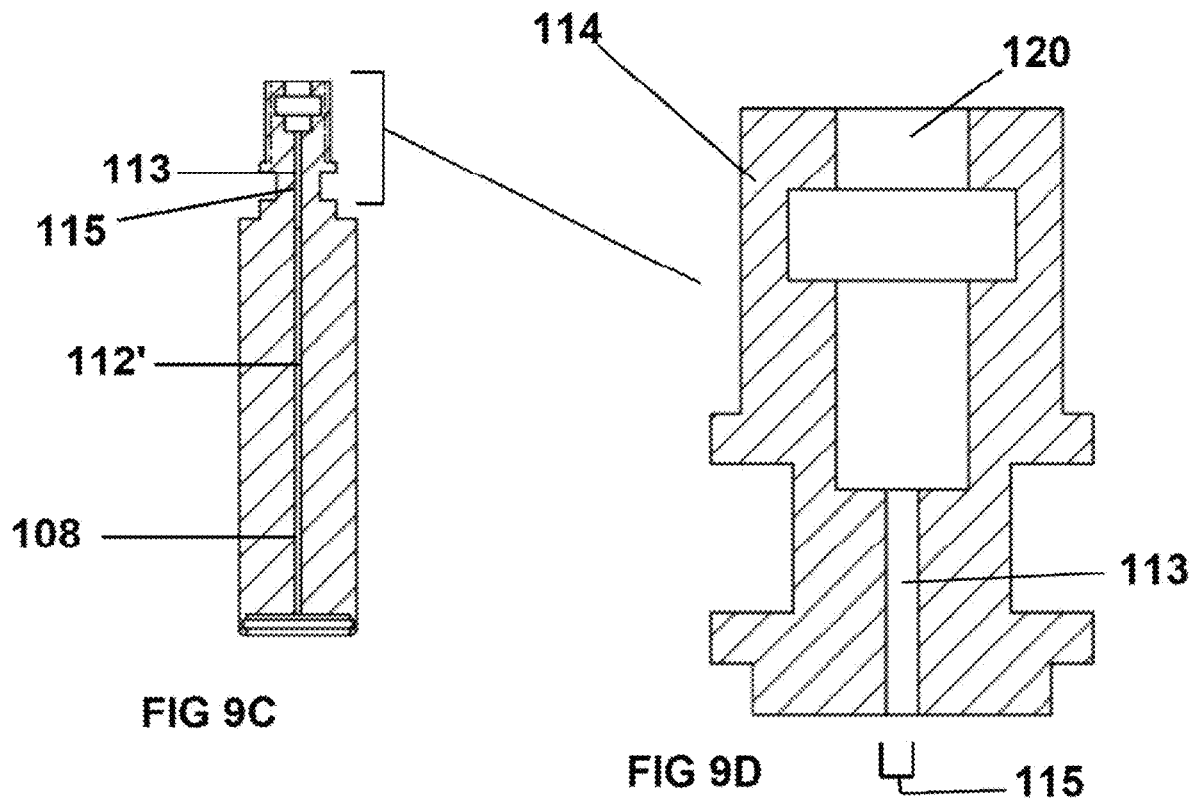
FIG 9A  FIG 9B  FIG 9C  FIG 9D

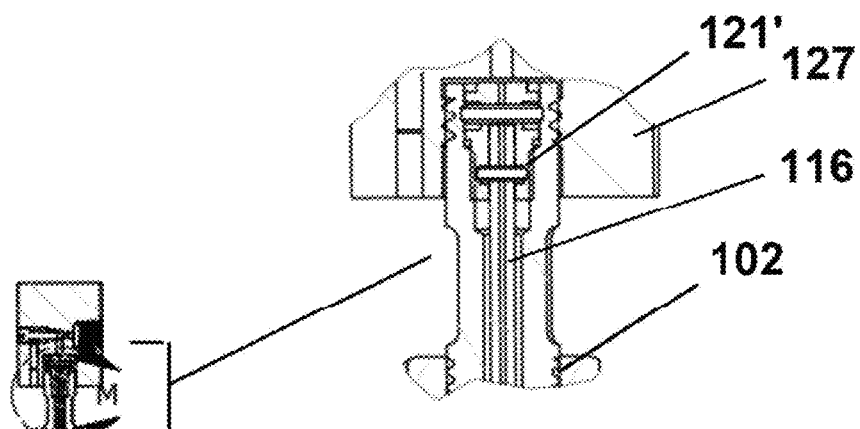
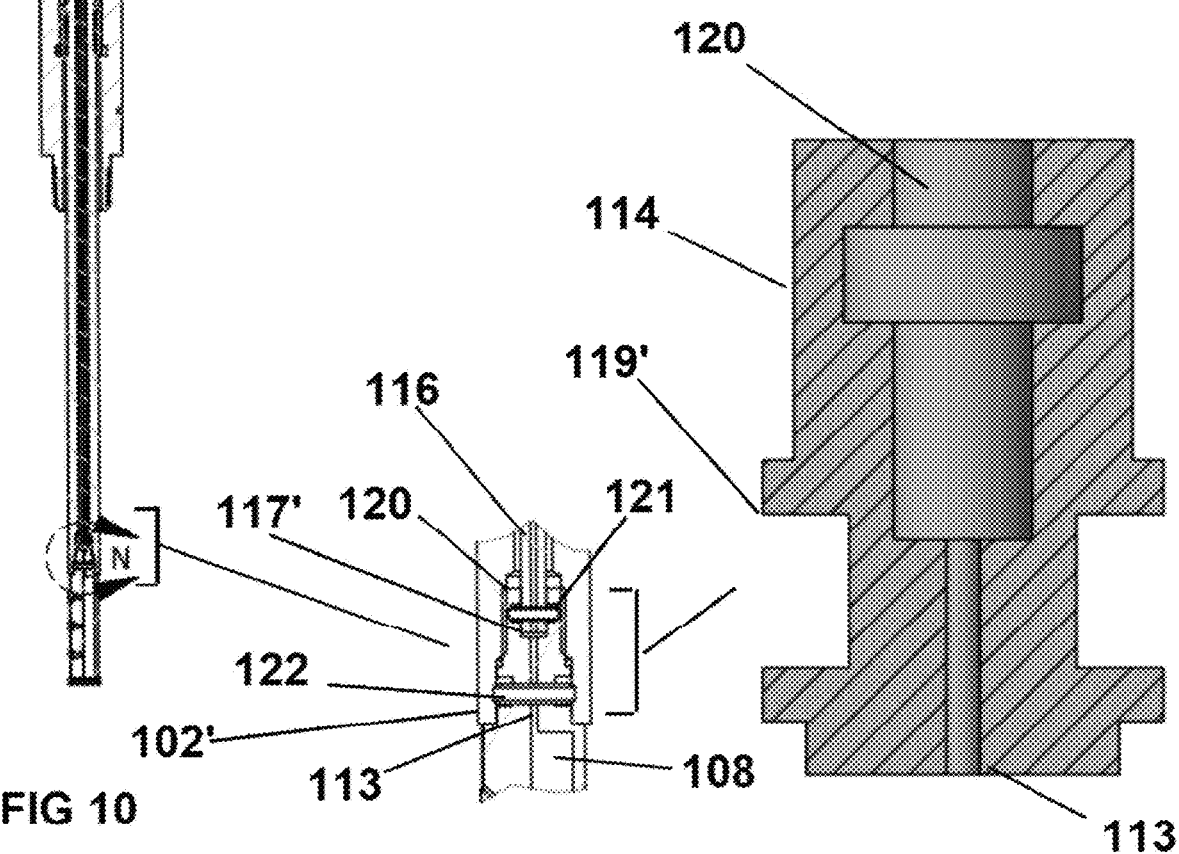
FIG 10A
FIG 10
FIG 10B
FIG 10C

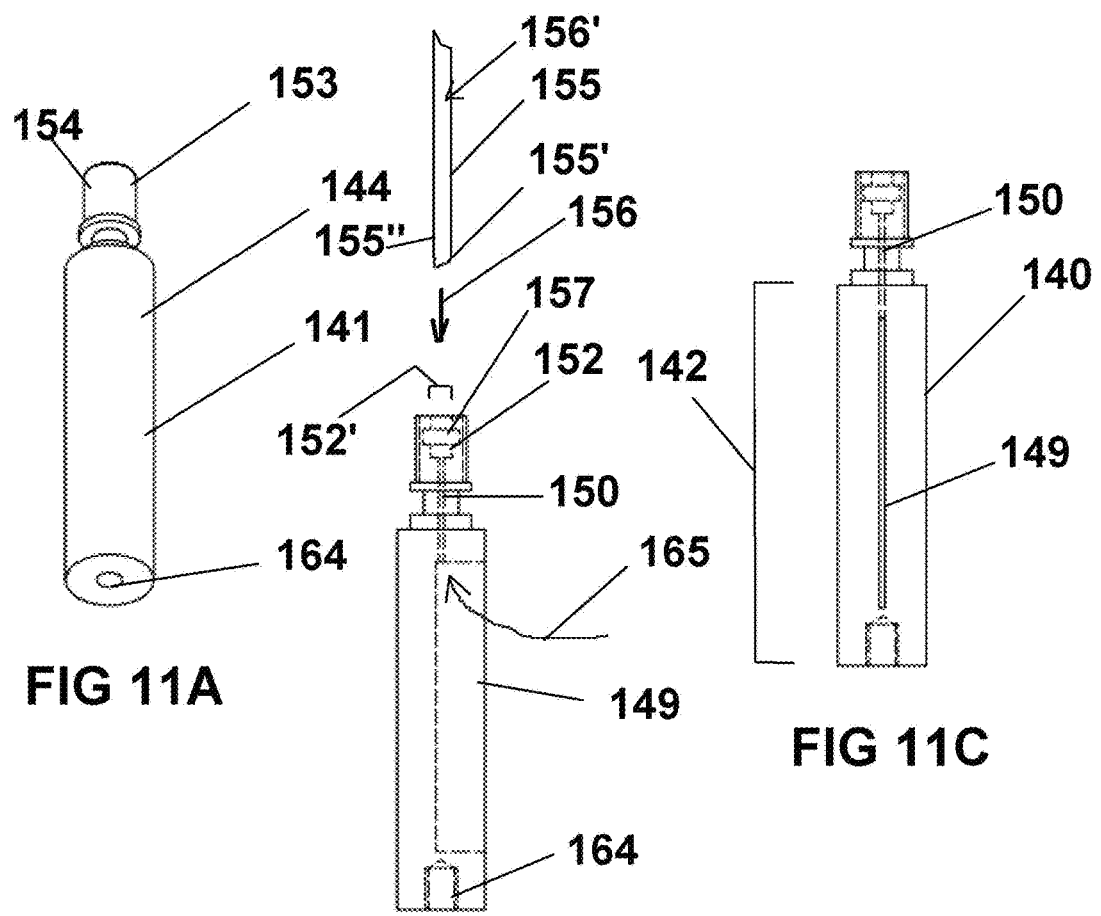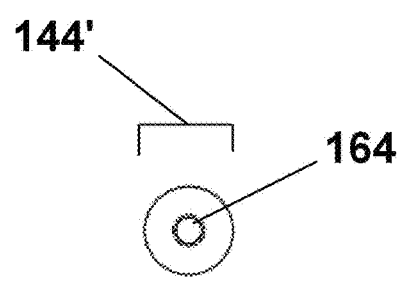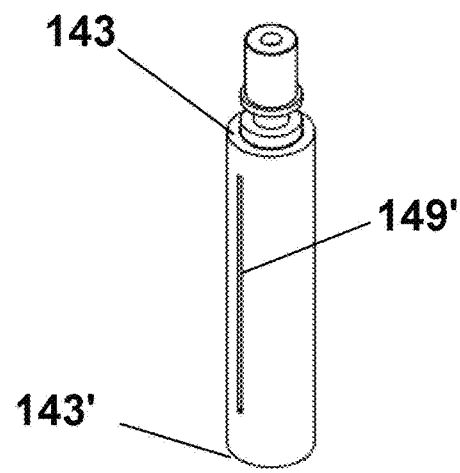

WET GAS LATERAL SAMPLING SYSTEM AND METHOD

The present application is a continuation-in-part of U.S. Utility patent application Ser. No. 14/214,225, filed Mar. 14, 2014, listing as inventor Valmond Joseph St. Amant, III, entitled "Wet Gas Lateral Sampling System and Method". The present application is also a continuation-in-part of U.S. patent application Ser. No. 15/615,786 filed Jun. 6, 2017, listing as inventor Valmond Joseph St Amant, III, entitled "Source Mounted Wet Gas Sample System. The present application is also a continuation-in-part of U.S. patent application Ser. No. 15/615,772 filed Jun. 6, 2017, listing as inventor Valmond Joseph St Amant, III, entitled "Wet Gas Sample System".

FIELD OF THE INVENTION

The present invention relates to sampling of pressurized process fluids, and more particularly a system for on-stream and/or spot sampling of pressurized process gas having liquid entrained therein, otherwise known and referenced as multiphase or "wet" such as natural gas or the like. The invention contemplates a unique probe having a slot formed along its length formed to take a linear sample of fluids, and is designed for taking such a sample at a predetermined area of said fluid stream, including the center-third in compliance with recent Bureau of Land Management (BLM) requirements. The present invention further contemplates the use of a screen or membrane provided exterior the probe tip body to block or lessen the likelihood of undesirable particulates or to block or lessen the likelihood of undesirable liquid contaminants such as glycol from entering the slot formed in the probe, yet allowing components of interest (liquid hydrocarbons).

BACKGROUND OF THE INVENTION

Natural Gas is comprised of a mixture of gases (See API 14.1 Section 6.3 and naturalgas.org). Natural gas is bought and sold based on its heating value (BTU), which is derived from a compositional analysis of the natural gas. It is the BTU content that determines the monetary value of a given volume of natural gas. This BTU value is generally expressed in decatherms (one million BTU).

To determine the total heat value of a given volume of gas, a sample of the gas is analyzed, and from the compositional data, its heat value per unit volume is calculated. This value is generally expressed in BTU/cu ft. The typical range of transmission quality gas ranges between 1000 and 1100 BTU/cu ft. Production gas, storage facility gas, NGL, and new found Shale Gas can have much higher heating values up to or even exceeding 1500 BTU/cu ft.

There has been a long-standing controversy between gas producers and gas transporters regarding entrained liquid typically present in most high BTU/cu ft. gas (rich or "wet" gas). Transporter tariffs require essentially liquid-free gas. Liquid in the gas being transported causes operational and safety problems. The practice is to separate the liquid before entering a transport (pipe) line.

The API 14.1 standards (Manual of Petroleum Measurement Standards, 2006) scope does not include supercritical fluid (dense phase) or "wet gas" "(a term referenced by the Natural Gas industry as a gas that is at or below its hydrocarbon dew point temperature and/or contains entrained liquid), nor does the GPA 2166 standard (Obtaining Natural Gas Samples for Analysis by Gas Chromatography, 2005). In summary, there is no known standard which defines how to obtain a "representative sample" of a natural gas supply having entrained liquid in any form.

Therefore, to fully comply with the current industry standards, membrane-tipped probes such as the A+ Corporation Genie Probe (see U.S. Pat. Nos. 6,357,304, 6,701,794, 6,904,816, 7,004,041, and 7,134,318) have been used for many years to shed entrained liquids inside pressurized pipelines. Companies such as Mustang Sampling, LLC have bolted enclosures to the A+ Corporation membrane-tipped probes. See for example patents Thompson U.S. Pat. No. 7,162,933, and Hess U.S. Pat. Nos. 4,821,905A, 4,889,235A, 4,307,264A Mustang Sampling, LLC Brochures MSB-PONY and MSB P53, available at their website, can include products incorporating A+ Corporation Genie membrane tipped probes, and utilize third party, electrically-powered heater blocks (for example, as provided by Intertec-Hess) and A+ Corporation cartridge-type heated regulators and third party heat traces, such as taught by Raychem U.S. Pat. No. 4,286,376A heat trace spliced together with splicing kits and connectors such as Protherm Industries and Pentair, as described above. Mustang Sampling brochure MSB P53 illustrates a product which can include A+ Corporation GENIE brand membrane separators (U.S. Pat. No. 7,555, 964, a CIP of 7097693 (listing the present Inventor as second Inventor)) in an enclosure, which is ideally mounted in the vicinity of the analyzer, which may include additional electrically-powered heater blocks and electrically powered heated regulators (See Mayeaux U.S. Pat. No. 6,357,304, Thompson U.S. Pat. No. 7,162,933, and Thompson US 2012/0325694 A1).

Other companies such as Welker Engineering use non-membrane probes (fixed probes) and bring the liquids outside the pipeline to reject the liquids inside enclosures containing an electrically powered heated regulator and then returning the liquid back to the pipeline, while hanging a hinged enclosure onto the probe (see Welker SCHS manual, page 6, at their website, and U.S. Pat. No. 7,471,882). The purpose of these sample systems is to reject ALL entrained liquids and maintain the sample system temperature above the sample dew point to prevent further condensation.

Recently the Bureau of Land Management (BLM) has revised 43 CFR 3175 (Order 5) The Onshore Oil and Gas Operations, Federal and Indian Oil and Gas Leases, Measurement of Gas effective Jan. 17, 2017, as indicated in the Federal Register, Vol 81, No 222, Sections 3175.111 and 3175.112, pages 81578-81580, issued 17 Nov. 2016.

Sections 3175.111 and 3175.112 now mandate a sampling protocol that is outside of the scope of API 14.1 and GPA 2166, by mandating sampling of two-phase samples (gas with entrained liquids) without rejecting the liquids, to provide a sample to the analyzer. The new BLM order tries to reference parts of API 14.1 and GPA 2166, but it is clearly outside the scope of both of those industry standards. In addition, the new BLM order forbids the use of membranes which could remove hydrocarbon components from the fluid sample and thereby change the hydrocarbon composition of the sample. The new order is further believed to require that liquids and gases be removed from the center third of the pipeline and heated sample lines to vaporize any liquids removed before they reach the analyzer.

GENERAL SUMMARY DISCUSSION OF THE INVENTION

The present system contemplates a unique probe suitable for taking a linear sample of fluids at the medial area (or elsewhere as desired) of said fluid stream. The unique design and method of operation makes it particularly suitable for BLM order 5, providing compliant sample probes and methodologies. The present invention is also uniquely designed to heat and vaporize the sample without the need for separate electrical power.

Unlike the above discussed, prior art sampling systems, the present invention teaches a new and innovative "integral slice" sampling process, wherein a very thin slice of the total volume of the source fluid flowing through a conduit or pipeline is captured by a streamlined container arrangement (in the preferred embodiment, a probe tip having an elongated passage forming a slot along its length) suspended in said source fluid, in a similar manner to an integral in calculus—a limiting procedure which approximates the area of a curvilinear region by breaking the region into thin vertical slices—with nominal flow disturbance, and in which trapped fluid is subsequently withdrawn and isolated in a location outside of the source fluid flowing stream.

Further, unlike dynamic isokinetic techniques, the system of the present invention insures that the representative sample taken either in spot, batch or continuous fashion is not allowed to disassociate due to the very small internal cavity of the slot and outflow passage following the slot. Empirical testing verifies that, if the diameter of the passage is sufficiently small, then the combination of capillary action (which is caused by cohesion within the liquid and adhesive forces between the liquid and container wall) and the higher velocity sweep will act to propel the liquid as well as the gas, preventing disassociation. The pipeline area is very large compared to the probe's very small interior and because of this vast difference; fluid in the probe will always be of a higher velocity than the pipeline fluid.

In the preferred embodiment of the present invention, the high gas velocity (higher than the source velocity of the pipeline) of the very small internal cavity would then sweep the all of the liquid particles at the same velocity as the gas particles being transported from the source to the probe. Therefore, it would remain "associated" with the gas from which it condensed. Small particles such as that which comprise smoke are known to behave somewhat like large molecules. High velocity gas in the small internal diameter bore of the probe will prevent any significant layer of liquid from accumulating on the surfaces. Even if an ultra-thin layer were to coat the probe's interior, the total area is so small that the impact would be negligible.

The present invention provides a far superior sampling solution for wet gas streams, including high HC dew point gases, which traditionally have been difficult to sample dynamically due to phase changes and resulting composition changes which can be triggered by flow, pressure, and/or temperature.

The inlet of the preferred embodiment of the sample probe of the present invention forms a fluid passage which is formed, taking into account the fluid composition of the fluid stream to be measured, utilizing the very small internal cavity which have capillary geometries so as to facilitate capillary motion for the fluid passing therethrough, while providing a higher flow velocity, so as to sweep all of the liquid particles along at the same velocity as the gas particles. In fact, it is the combined effect of these two traits, that is, enhanced flow velocity, coupled with capillary effect, which makes the slip ratio infinitesimally small, facilitates the sweeping action which is unique to this system. Accordingly, the tubing geometry AND the decrease in passage size works in concert to facilitate an enhanced pass-through of the gas with entrained liquid so as to prevent disassociation, that is, the capillary geometry of the tubing (hereafter "capillary tubing") of the present invention will not allow a two-phase sample to disassociate as it is transported therethrough.

The capillary tubing of the sample probe of the preferred embodiment of the present invention may be in the form of a passageway formed in the probe, or in the form of an insert formed to engage a passageway in a probe, said passageway may be of conventional size, the insert converting the probe to a capillary probe, facilitating capillary action for fluid containing entrained liquids flowing therethrough, a higher velocity, for enhanced sweeping action and optimal slip ratio.

Through empirical testing, it has been determined by the present inventor that less than 1/32" inner diameter has consistently provided capillary action flow characteristics in the present wet gas application, although the optimal specific geometry can vary depending on a number of criteria. A combination of phase diagram data and empirical testing could be used as a guide to determine the optimum capillary diameter/geometry for the particular wet gas composition, taking further into account the particular pipeline/flow, property/application/environmental and other factors.

The present invention further contemplates the use of a screen or membrane provided exterior the probe tip to block or lessen the likelihood of undesirable particulates or to block or lessen the likelihood of liquid contaminants such as glycol from entering the slot formed in the probe, yet allowing the passage therethrough of components of interest (liquid hydrocarbons). It is has been empirically tested and shown that, with the use of a polymer membrane (for example, the Type 8 membrane provided by A+ Corporation of Gonzales La.) upstream the probe opening, liquid non-hydrocarbon contaminant additives such as glycol can be blocked from entering the probe, while allowing the passage of the full hydrocarbon fluid content therethrough to the probe.

To prevent sample distortion after passing through the membrane (which can result in a decreased flow velocity) the use of capillary passage to facilitate flow through the probe in the present invention is designed to result in capillary action in the flow therethrough, preventing disassociation of two-phase flow content, thereby maintaining the compositional content of the fluid stream sample for conditioning, collection and/or analysis.

Alternatively, the slot and any passages downstream can be formed to facilitate the flow of wet gas therethrough at least at the velocity of fluid entering the probe (e.g., without reduction in flow velocity), which could also maintain the compositional content of any wet gas flowing therethrough where capillary passage might not be practical or desirable.

BRIEF DESCRIPTION OF DRAWINGS

For a further understanding of the nature and objects of the present invention, reference should be had to the following detailed description, taken in conjunction with the accompanying drawings, in which like parts are given like reference numerals, and wherein:

FIG. 1A is a side, perspective frontal view of the slotted probe tip of the first embodiment of the present invention, which is particularly suitable for use in continuous mode sampling, such as with on-line analyzers and the like.

FIG. 1B is a side, perspective view of the embodiment of the slotted probe tip of FIG. 1, illustrating the probe lowered into a pipeline containing a process gas stream containing entrained liquid or the like.

FIG. 8A is a rear view of an embodiment of the probe of FIG. 7A, illustrating a series of tapped holes or screws situated in spaced relationship along the length of the rear of the probe, for holding an optional screen filter sized to prevent solid particulates from entering the slot.

FIG. 8B is a perspective view of the invention of FIG. 8A, illustrating the position of the forward sampling slot in relation to the tapped holes.

FIG. 8C is a greyscale view of the invention of FIG. 8B.

FIG. 8D is a bottom, partially cutaway view of the invention of FIG. 8A.

FIG. 9A is a close-up, frontal view of the invention of FIG. 7A.

FIG. 9B is a greyscale view of the invention of FIG. 9A.

FIG. 9C is a side, partially cut-away, partially cross-sectional view of the invention of FIG. 9A.

FIG. 9D is a side, partially cut-away, partially cross sectional, detailed view of the threaded end of probe 114 and outflow passage 113 of FIG. 9C.

FIG. 10 illustrates a side, partially cut-away, partially cross-sectional view of the probe with slotted probe tip of the present invention having the capillary line through the length of the probe via probe passage, passing through the probe first end, rack, and the second end to probe tip.

FIG. 10A is a side, partially cut-away, detailed view of the first end of the capillary tube engaging a flow component for flow out of the probe, sealed via O-Ring.

FIG. 10B is a side, partially cut-away, detailed view of the second end of the capillary tube engaging a receiver formed within the threaded area of the slotted probe tip of the present invention, via sealed O-rings.

FIG. 10C is a cross-sectional, close-up, side view of the receiver formed to receive the capillary tube in the threaded area of the slotted probe tip.

FIG. 11A is a rear, perspective view of the third embodiment of the slotted probe tip of the present invention, illustrating the threaded aperture formed at the second end of the body for receiving a threaded fastener for securing a cylindrical gas permeable membrane and related mounting hardware about the body of the unit.

FIG. 11B is a side, view of the invention of FIG. 11A, illustrating in phantom the outflow passage and outlet at the first end of the body, slot formed along the length of the body from the central longitudinal axis of the body to the front, and threaded aperture formed at the second end of the body.

FIG. 11C is a front view of the invention of FIG. 11A, illustrating the opening formed along the length of the body by the slot formed therein, with the outflow passage shown in phantom.

FIG. 11D is a side, perspective view of the invention of FIG. 11C.

FIG. 11E is a bottom view of the invention of FIG. 11D, illustrating the threaded aperture formed at the second end of the body and the outer diameter (OD) of the body of the slotted probe tip.

DETAILED DISCUSSION OF THE INVENTION

Figure 2A:
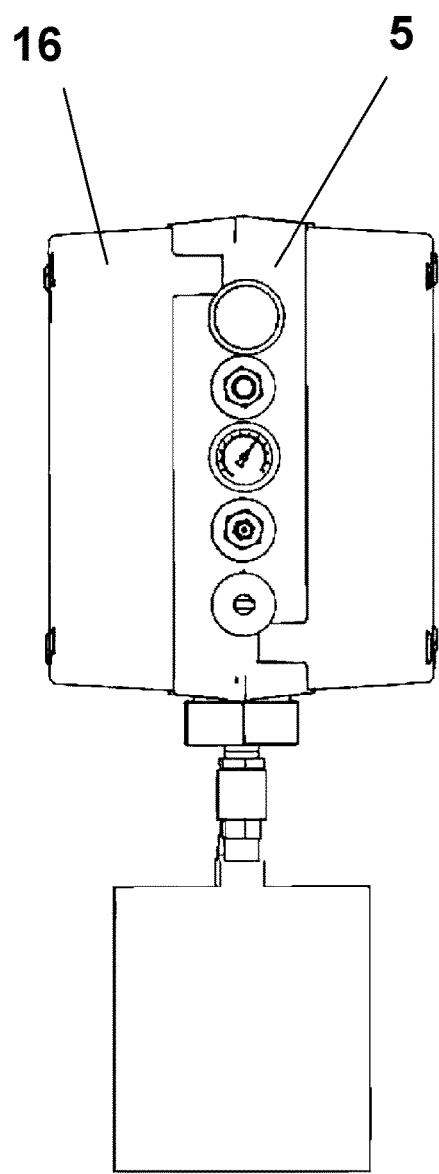
FIG. 2A is a frontal view of a modular sample conditioning system comprising modular sampling and/or conditioning components mounted to a substrate bracket, enclosed via a housing/enclosure.

First Embodiment of the Invention—Continuous Sampling for On-Line Analyzers

Referencing FIGS. 1A-1B, the device of the present invention contemplates a sample collection apparatus for use collecting a fluid sample from a fluid stream F in a pipeline L or the like. In the preferred embodiment of the present invention, the apparatus is in the form of a sample collection apparatus C in the form of a slotted probe tip 48, shown mounted to an insertion probe P, the probe tip 48 comprising a body 31 having a length 32 forming a longitudinal axis 35 and terminating in first 33 and second 33' ends. As the body 31 in the present embodiment shown is in the form of a cylinder (although this may vary with application), the outer wall 34 forms an outer diameter 34' of the body.

Formed through the outer wall 34 and part of body 31 is an elongated, continuous or uninterrupted elongated opening 36 or slot S having a length 37 aligned with the longitudinal axis 35 of the body 31, the opening 36 having a relatively narrow width 37', and opposing first 40 and second 40' ends to provide the entrance to slot 38, the slot forming first 41 and second 41' side walls within the body having an outer edge 42 and an inner edge 42' corresponding to its depth 38', the slot forming a passage communicating with outflow passage 43 having a small inner diameter 45 as shown (preferably less than 1/32" ID, as will be further discussed, infra).

In the preferred embodiment of the invention shown in the figures, the slot 38 preferably has a relatively uniform width corresponding to that of opening 36, while providing passage to the central axis 39 of the body 31 at the inner edge 42' of the slot, or about halfway through body 31. The slot as shown runs along the central axis 39 of the body 31, which corresponds to the longitudinal axis 35 of its cylindrical configuration forming the collection apparatus C, although the length and position of the slot can vary depending upon the application.

As shown, the slot 38 runs from just below the first 33 end of body 31 to about the second end 33' of body 31, with the inner edge 42' of the slot 38 engaging and providing passage to outflow passage 43 at second 44' end, the first end 44 of outflow passage 43 at the first, upper end 33 of body 31, said first end 44 of outflow passage 43 having a small inside diameter 45, as shown, which is formed to provide passage, as required fluid flowing from the slot, through the outlet passage 43, and effectively through probe P', the outflow passage 43 in the present embodiment preferably having an inner diameter 45 having a cross sectional area no greater than the area associated with the elongated opening 36 forming the slot S, so as to avoid reduction of fluid velocity as fluid passes through the probe.

The present system is formed to collect via the slot in the slotted probe tip a "linear sample" spanning the diameter of the pipe, from side-wall to side-wall, or in this case from top to bottom, providing a representative sample of fluid the fluid stream wherein a fluid sample of the fluid stream is collected along a line spanning the inner diameter of said pipe, even where there is present entrained liquid particles and even flowing liquid droplets/streams along the lower and/or upper surfaces of the pipe. While the present figures illustrate the position of the probe tip as vertical, this is not intended to be limiting, as the probe can be oriented at any angle relative the pipe, as long as the probe interface (insertion point) allows it.

The slot and outflow passage are preferably relatively narrow (less than 1/32" depending on the volume of fluid being sample, the speed, viscosity, and other factors) to remove a very thin slice of the total breadth of the fluid stream, so as to provide an accurate composite of the total fluid flow using principals similar to the integral principle as used in calculus.

As described, the body forming the probe has a first and second ends defining a length therebetween, with a slot defining a narrow opening to a centrally disposed outflow passage of preferably equal or less internal diameter than the slot width, said outflow passage preferably of equal or less area than the slot area, thus providing the "integral slice" (in the present example, less than 1/32" wide slot from the outer surface of the probe) to intersect the small ID outflow passage (less than 1/32"), so that process fluid having sample gas containing entrained liquid therein passes into the slot then is urged through the outflow passage to the probe at an equal or higher velocity than the fluid stream, so as to preserve the composition of the fluid stream and prevent disassociation of same.

The "linear sample" forming the integral can, depending on the circumstances, be taken at varying lengths, by changing the probe tip to vary the length of the slot formed therein. FIG. 1B shows the probe having a length with slot corresponding to the maximum internal diameter (ID) of the process pipeline. In the embodiment illustrated in FIG. 1B, the collected sample would typically flow to a heated zone H to vaporize any liquids, providing a single phase sample, then to a process analyzer A and/or, monitor, sample container, or other end use. Other embodiments in the present application show a probe tip sized and positioned to collect a sample from the center third of the pipeline, as required in some circumstances (such as certain BLM applications).

Continuing with FIGS. 1A and 1B, the system of the present invention insures that the representative sample taken either in spot, batch or continuous fashion is not allowed to disassociate by providing the very small internal cavity forming the outflow passage, to maintain or enhance the fluid flow velocity through the system. The pipeline area is very large compared to the probe slots' very small interior and because of this vast difference, fluid in the outflow passage from the slotted probe tip to the probe will always be of a higher velocity than the pipeline fluid.

The high gas velocity (higher than the source velocity of the pipeline) of the very small internal cavity/fluid outflow passage is formed to sweep all of the liquid particles at least at the same velocity as the gas particles being transported from the source to the probe. Therefore it would remain "associated" with the gas from which it condensed. High velocity gas in the small internal diameter bore forming outflow passage engaging the relatively narrow slot of the probe will prevent any significant layer of liquid from accumulating on the surfaces. Even if an ultra-thin layer were to coat the probe's interior, the total area is anticipated to be small that the impact would be expected to be negligible.

Along with the higher velocity sweeping the wet gas sample so that it does not disassociate, conventional science recognizes that, as the inside diameter or cross sectional area of a slot or passage decreases, a static liquid having sufficient surface tension will interact with the walls of sufficiently small slot or passage to trigger capillary motion, a phenomenon known to occur when the static liquids adhesion to the walls is stronger than the cohesive forces between the liquid's molecules. Such a phenomenon, in combination with the higher velocity sweep, is believed to be an inherently motivating feature in the present invention when wet gas passes through the slot or wall when the clearance is equal to or less than 1/32", although the exact threshold where static capillary function can and will occur in this dynamic sweeping combination can vary depending on the composition of the wet gas, environmental factors, as well as other factors.

Continuing with the figures, as shown, the slotted probe tip 48 of the present invention is engaged to the end of an insertion probe V then is lowered 46 into a pipeline L until the second, lower end 33' of the body 31 is situated in the vicinity of the opposing inner sidewall (in this case, the bottom) of the pipe containing a process gas stream F containing entrained liquid, with the opening 36 forming the entrance of the slot 38 facing the flow stream.

A portion of the fluid stream comprising a "linear slice" comprising the diameter of the pipe (in the present example, other examples might only collect the center third as discussed herein) then passes into the opening, into and through the slot, then through the pressure of the flow stream is urged through the outflow passage for heating and/or collection, online analysis, monitoring, or other usage. As earlier indicated, the outflow passage 43 in the present embodiment preferably has an inner diameter 45 commensurate with or less than the width of the slot formed in the body forming the slotted probe tip, resulting lesser area than the slot, so as to facilitate at least equal but more likely greater fluid velocity flow through said outflow passage (depending on the size), to maintain flow velocity of the fluid passing therethrough, to prevent slowing and possibly disassociating.

FIG. 1B illustrates the flow path of a "lateral slice" taken by the slotted probe tip of the present invention, wherein the flow through a pipeline spanning the entire internal diameter along a line from top to bottom of the ID of the pipe, and substantially along the entire length of the slotted probe tip, and thereby ideally encompassing all strata present in the fluid flow.

Continuing with FIGS. 1A & 1B, the second, lower end 33' of the body 31 forming the slotted probe tip is shown spanning the diameter of the pipe so as to engage the top and the bottom of the pipeline. Fluids flowing along the bottom of the pipe therealong are collected via the sample slot along with aerosols and gas comprising the flow stream spanning the diameter of the pipe, so as to provide the most accurate "slice" of the flow through the pipeline. The elongated opening 36 of slot would preferably be positioned directly facing the fluid flow stream, the sample flowing straight through the slot to the outflow passage 43.

While the above examples show the slotted probe tip of the present invention having a slot having a length formed to collect a sample from substantially the inner diameter of the pipe, the present invention is certainly not limited to that sampling functionality. As discussed, the present invention is specifically designed to have the flexibility of being able to provide a linear sample of all or a portion of the diameter of the pipe by simply choose the appropriate length of the slot forming the collection opening in the probe tip 48, and positioning same to the desired sample area using the insertion probe P'.

Accordingly, probe tip of the present invention can be made to provide a slot length as required, whether it be the full diameter (as shown in FIG. 1B), or in the case where the probe tip has formed therein a collection slot having a length comprising 1/3 the ID of the pipe (as will be further discussed herein), and as such could be positioned in the pipe to facilitate a sample of the center third of the fluid stream, as is required in some of the new BLM (Bureau of Land Management) sampling specifications, as will be further described herein.

Second Embodiment—Slotted Probe with Capillary Function

Like the first embodiment, the sample conditioning system of the Second Embodiment of the present invention (FIGS. 2A-10E) is mounted at the source of the sample, in this case a pipeline having pressurized process gas.

In an exemplary application, substrate coupling 4 is provided to provide a base for connection of the process flow to the modular sample system 5. The substrate coupling is mounted to a process isolation valve 3. The coupling 4 connects the process source 1 to a modular sample conditioning system 5 for conditioning the sample. Enclosure 16 is engaged to and supported by the substrate coupling 4, and is provided to house and protect the modular components (as further discussed herein). FIG. 3 is a cutaway view of FIGS. 1-2.

FIGS. 2A-6 shows pressurized source of gas (a/k/a process source) with entrained liquids 1 with the linear, slotted sampling probe tip 2 positioned in the fluid stream so that the collection slot 108 faces the fluid flow (FIG. 2B), the probe tip shown position in the center-third area to sample the center-third 21, medial area of the flow stream, although the probe length and associated collection area can be modified to provide different length linear samples as required. As shown, a process isolation valve 3 is provided to selectively open and close the flow from the probe to the modular sample conditioning system 5, as required.

Figure 2B:
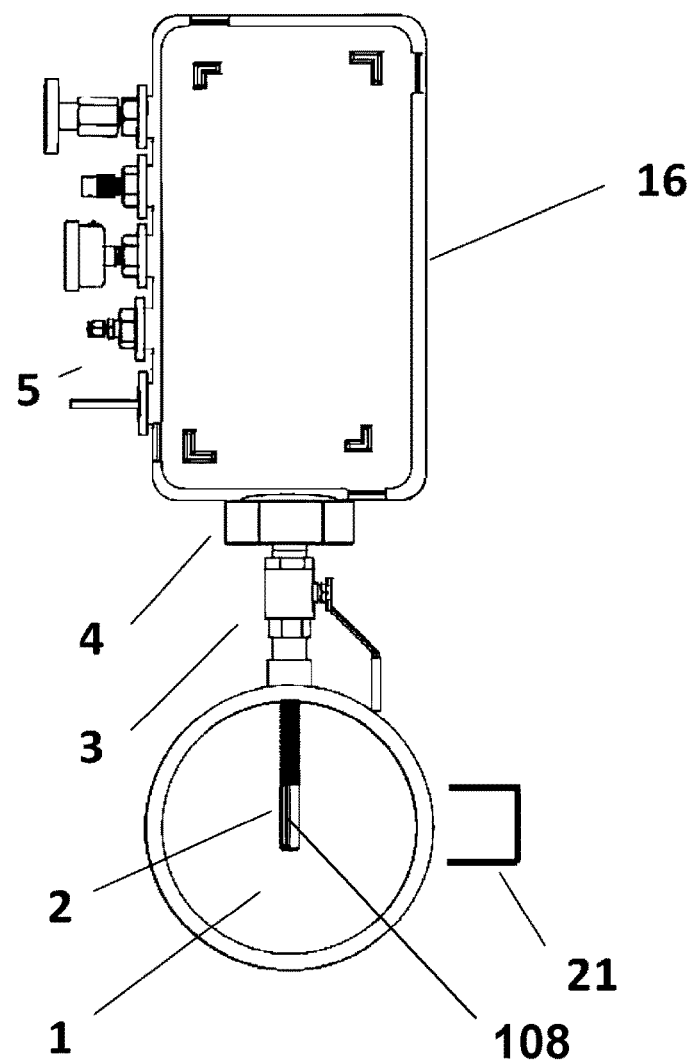
FIG. 2B is a side view of the invention of FIG. 2A, further showing an end view of the source of gas with entrained liquids, a linear sampling probe of the present invention situated therein, providing a passage to the modular sampling/conditioning components via substrate coupling 4.
Figure 3:
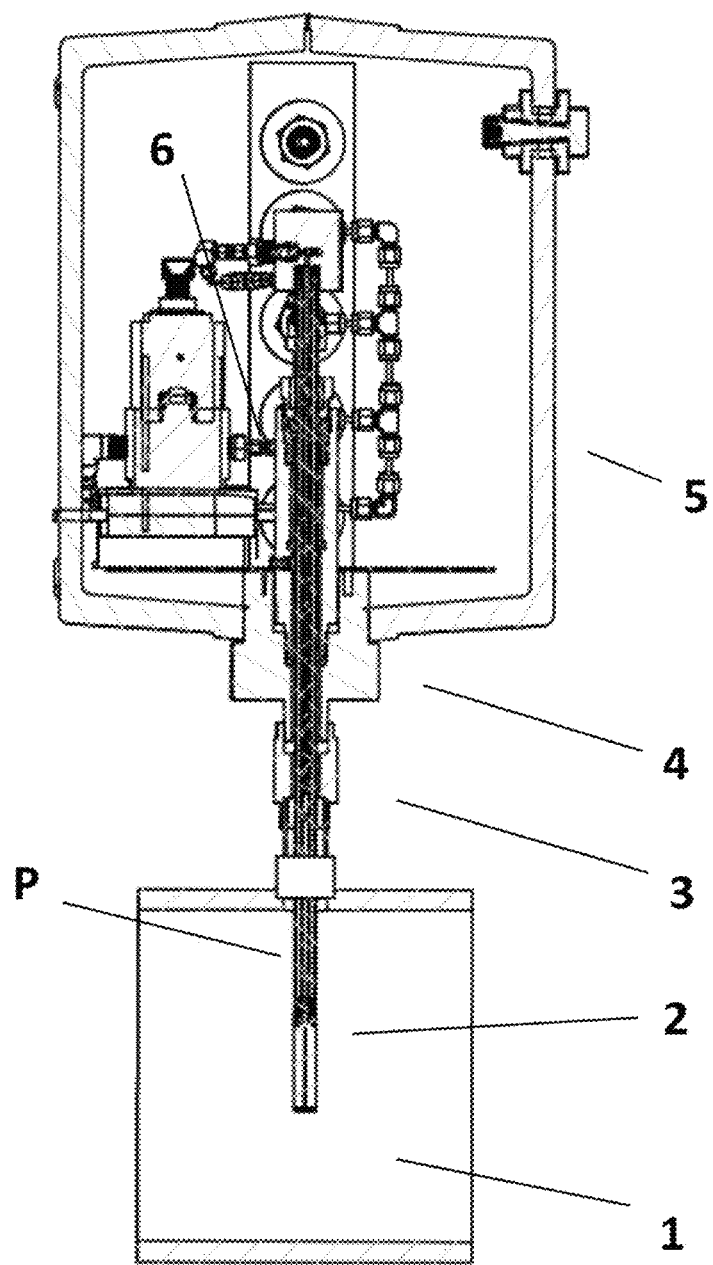
FIG. 3 is a rear, partially-cut-away view of the invention of FIGS. 2A-2B, illustrating the linear sampling probe and substrate coupling of the present invention, to prevent the disassociated collection of gas having entrained liquids therein.
Figure 4:
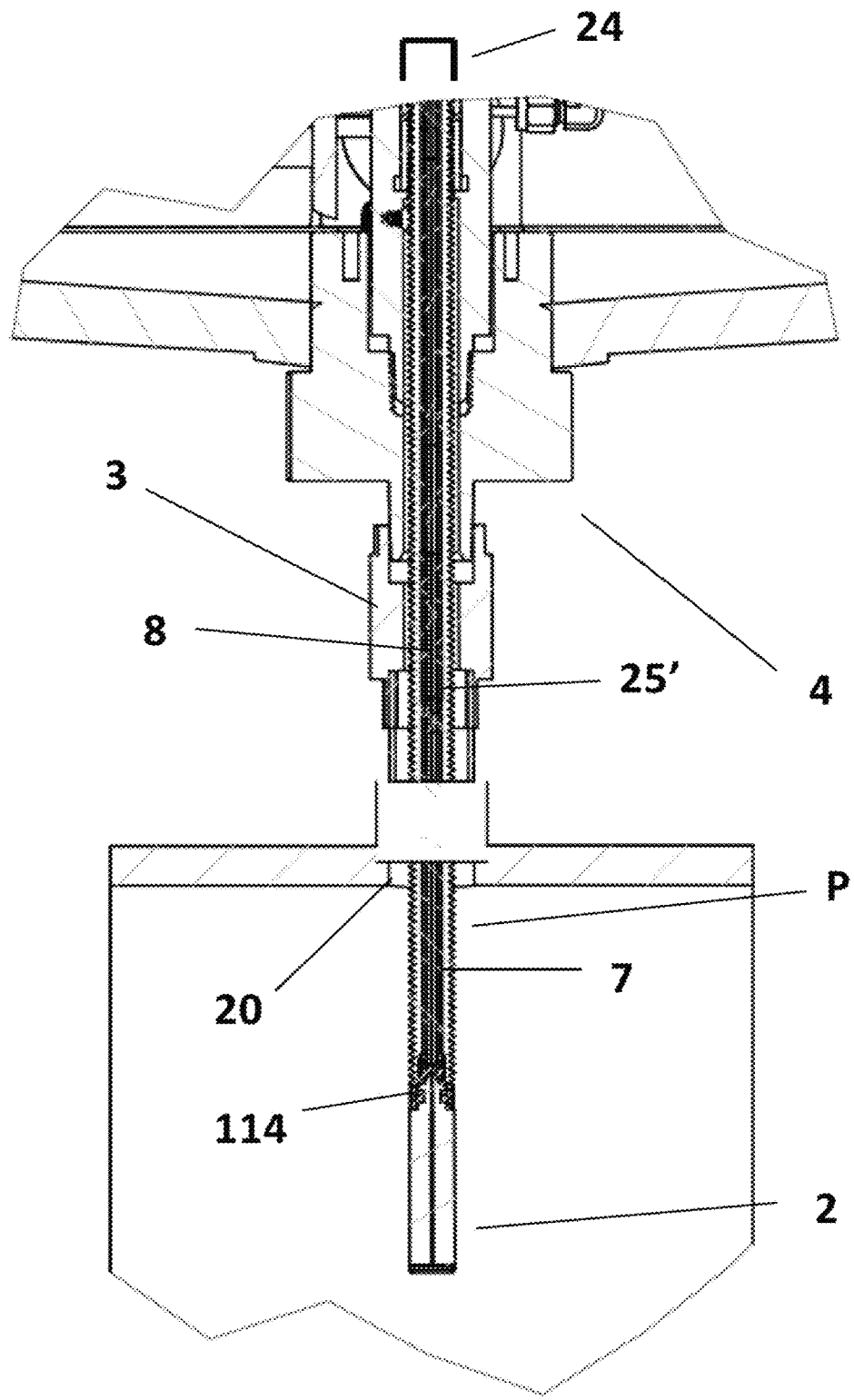
FIG. 4 is partial, close-up view of the probe and substrate FIG. 3.
Figure 5:
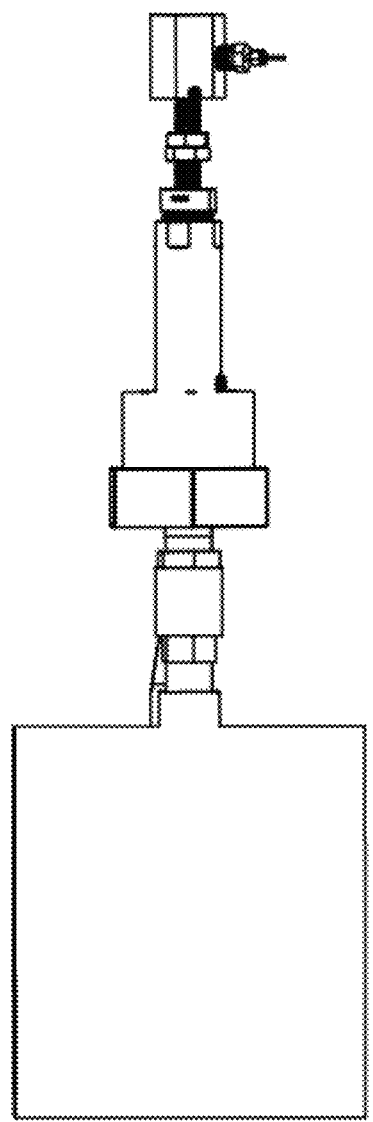
FIG. 5 is a side view of a pipeline containing a process gas flow having a linear sampling probe mounted thereto to sample the contents therein.
Figure 5A:
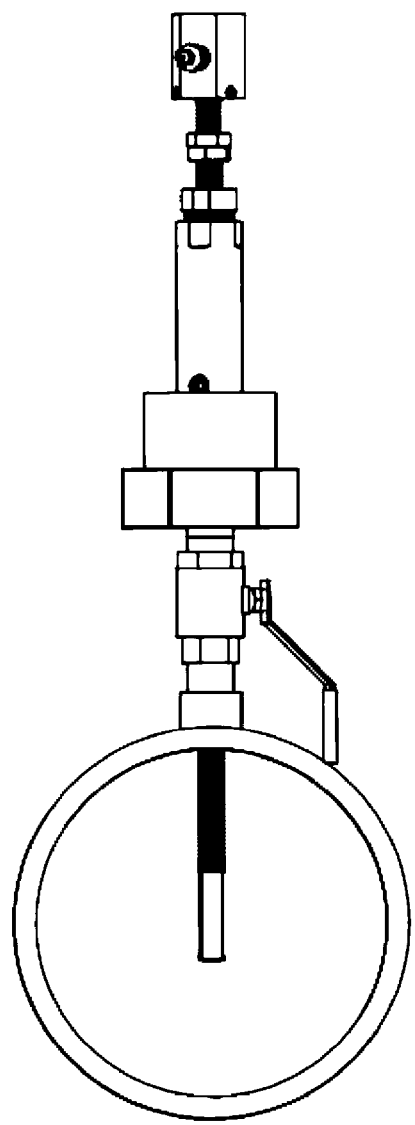
FIG. 5A is an end view of FIG. 5 showing the linear sampling probe with probe tip positioned at the center-third, medial area of the pipeline, so as to provide a center-third, medial sampling of same.
Figure 6:
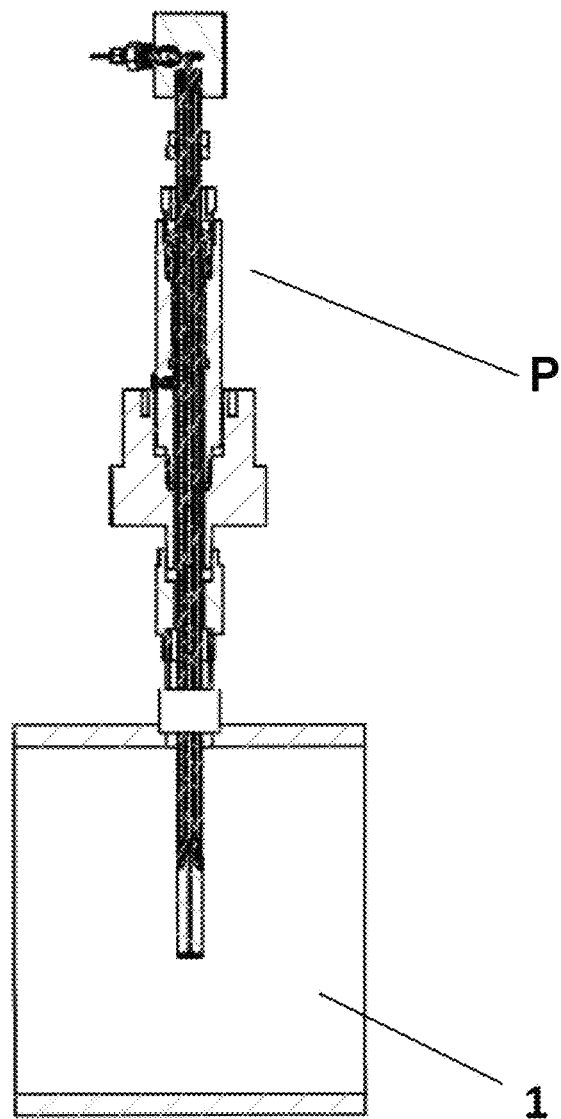
FIG. 6 is a side, sectional, cut-away view of FIG. 5A showing the insertion mechanism supporting the probe tip.
Figures 7A, 7B:
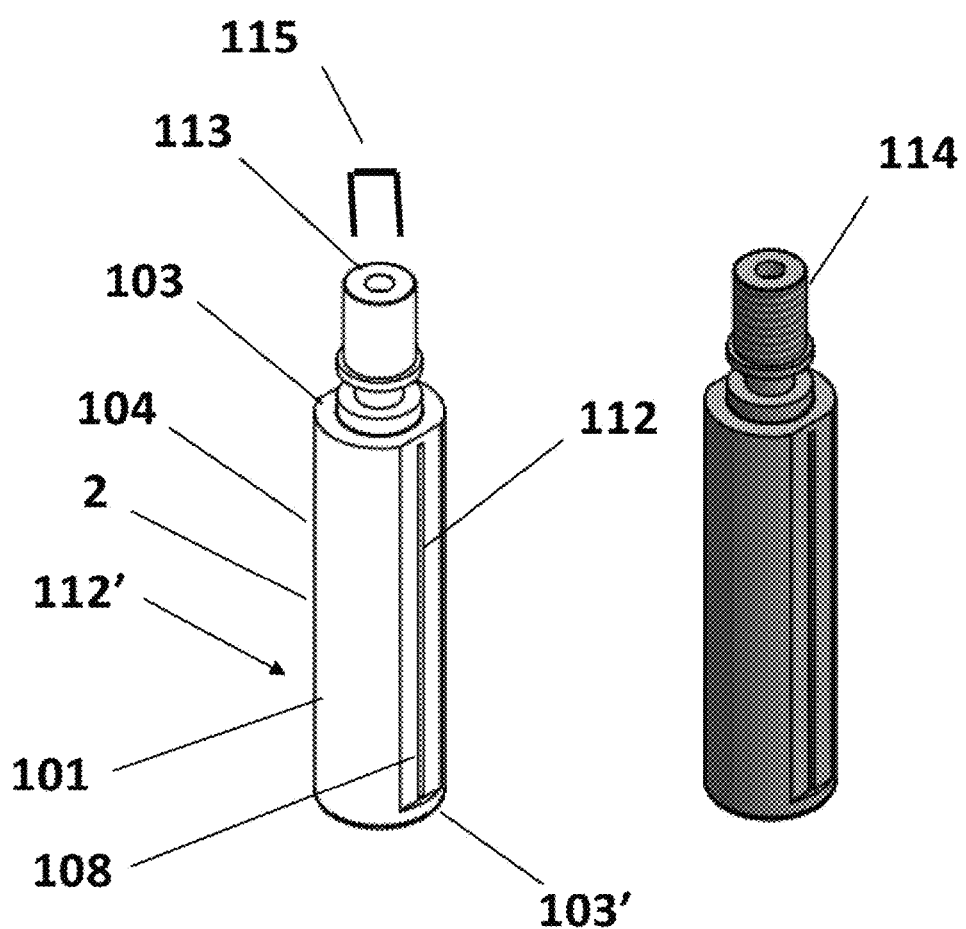
FIG. 7A is an isometric, front view of the second embodiment of the probe of the present invention, illustrating the linear slot formed along the length of the body and threaded connection end with capillary passage.
FIG. 7B is a greyscale view of the probe of FIG. 7A.
Figures 10D, 10E:
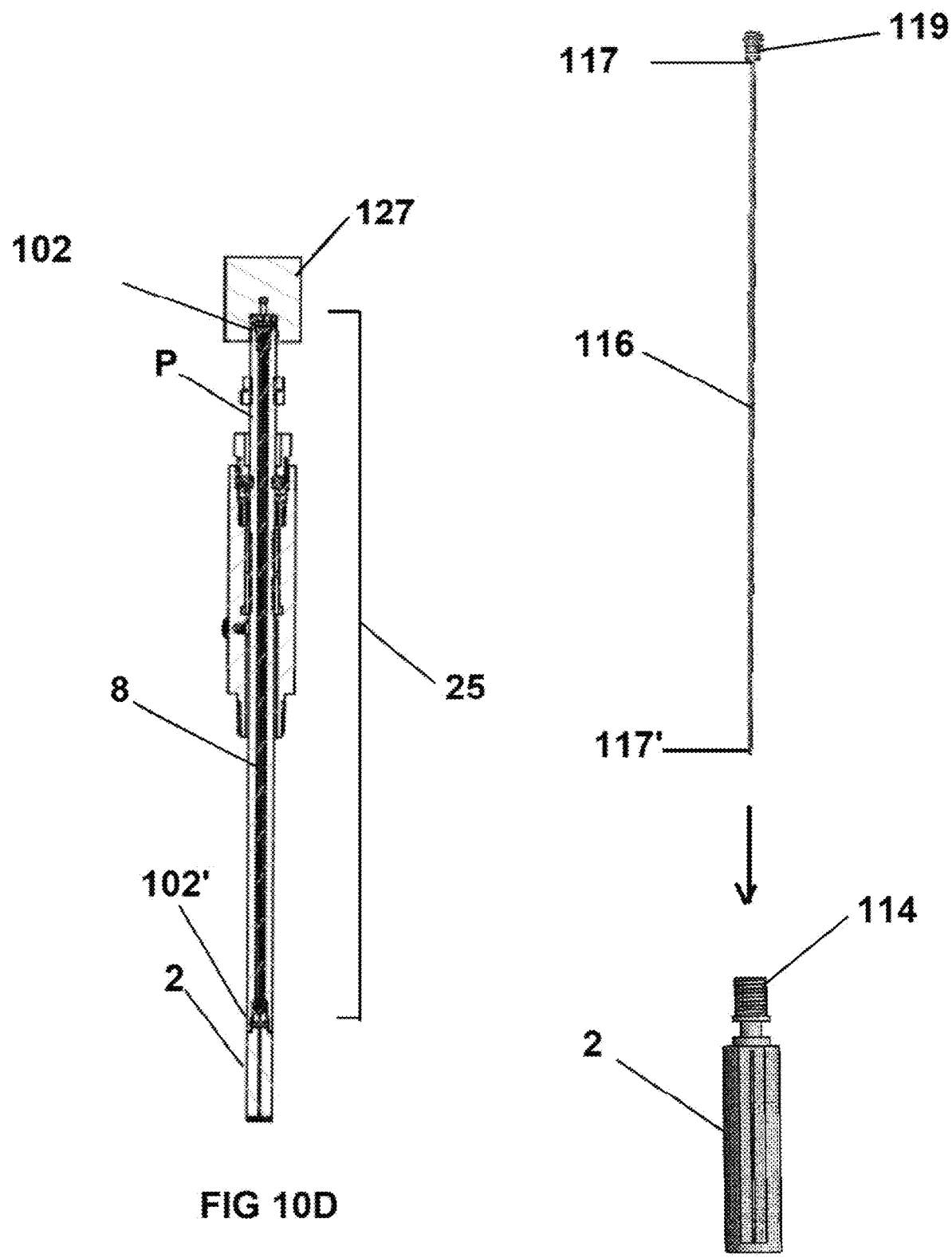
FIG. 10D is a side frontal, partially cut-away, partially cross-sectional view of the probe with slotted probe tip of FIG. 10.
FIG. 10E is a side frontal view of the probe tip of the present invention, illustrating the capillary tube aligned for insertion therein (the capillary tube will be positioned to pass through the probe to the probe tip as will be discussed herein).

Continuing with FIGS. 2A-10E, As shown, the probe P has a length 25 and first 102 and second ends 102', as will be further discussed herein. For insertion, a rack 25' may be provided along the probe P length as shown in FIG. 4.

Referring to FIGS. 7A-10E, formed through the outer wall 104 of body 101 of linear sampling probe tip 2 is an elongated, continuous or uninterrupted opening 106 having a length 107 aligned with the longitudinal axis 105 of the body 101, the opening 106 having a relatively narrow width 107', and ends 110, 110' to form a slot 108 penetrating the outer wall or surface of the body, the slot forming first 111 and second 111' side walls within the body forming an outer edge 112 and an inner edge 112' corresponding to its depth and providing a passage to outflow passage 113 having a small inside diameter as shown.

In the preferred embodiment of the invention shown in the figures, the slot 108 preferably has a relatively uniform width 107' preferably corresponding to, or less than, that of opening 106, while providing passage about to the longitudinal axis 105 of body 101, at the innermost edge 112' of the slot, about halfway through body 101. The slot as shown situated along longitudinal axis 105, although the length and position of the slot can vary depending upon the application.

As shown, the slot 108 in the exemplary, preferred embodiment of the probe tip of the present invention runs from just below the first 103 end of body 101 to about or just above the second end 103' of body 101, with the inner edge 112' of the slot 108 engaging outflow passage 113 having a small inside diameter 115, as shown, which is formed to engage, as required, (FIG. 3) insertion probe P to provide a channel of flow of fluid therefrom, the outflow passage 113 in the present embodiment preferably having an inner diameter 115 preferably equal to or less than the width 107' of slot.

The present system is formed to collect via the slot in the slotted probe tip a "linear sample" spanning a pre-determined area for sampling of the pipe, in the preferred embodiment of the present invention, the center-third area of the flow as is illustrated in FIG. 2B or (in other versions) alternatively other zones or even the full span of the diameter of the pipe (as shown in the first embodiment), so as to provide a representative sample of fluid the fluid stream wherein a fluid sample of the fluid stream is collected along a line spanning the inner diameter of said pipe, even where there is present entrained liquid particles and even flowing liquid droplets/streams along the lower and/or upper surfaces of the pipe. While the present figures illustrate the position of the probe tip as vertical, this is not intended to be limiting, as the probe can be oriented at any angle relative the pipe, as long as the probe interface (insertion point) allows it.

The slot and outflow passage are preferably relatively narrow (less than 1/32" depending on the volume of fluid being sample, the speed, viscosity, and other factors) to remove a very thin slice of the total breadth of the fluid stream, so as to provide an accurate composite of the total fluid flow using principals similar to the integral principle as used in calculus.

As described, the body 101 has first 103 and second 103' ends defining a length 107 therebetween, with a slot 108 defining a narrow opening to a centrally disposed outflow passage 113 of preferably equal or less diameter than the slot width, thus providing the "integral slice" (in the present example, less than 1/32" wide slot from the outer surface of the probe) to intersect the small ID outflow passage (less than 1/32"), so that process fluid having sample gas containing entrained liquid therein passes into the slot then is urged through the outflow passage to the probe at an equal or higher velocity than the fluid stream, so as to preserve the composition of the fluid stream and prevent disassociation of same.

Continuing with FIGS. 2A-10E, the threaded end 114 of slotted probe tip 2 threadingly engages the second end 102' of probe P. Probe P has a passage 8 formed therethrough along its length, the probe P having an outer diameter 24 formed allow its length to pass through isolation valve 3 (while in an open position) for selective insertion of the probe tip through isolation valve 3, and into the fluid stream in pipe via passage 20.

The probe has formed therethrough along its length probe passage 8 to provide for the passage of fluid from the probe tip 2 there through. In the preferred embodiment of the present invention, a capillary tube 116 (in the present embodiment, formed of stainless steel) is provided having a length and first 117 and second ends 117' and is situated through the length of probe passage 8, the second end 117' of capillary tube 116 formed to engage the outflow passage 113 of probe tip 2 at a receiver 120 formed within the threaded area 114 of probe tip 2, the first end 117' of capillary tube 116 sealingly engaging the probe tip's outflow passage 113 via first O-ring 121. The second end 102' of insertion probe P engages the probe tip 2 via O-ring 122 at retainer 119', providing sealed connection.

The capillary tube 116 in the present embodiment passes through the length of probe passage 8, the O-ring 121' at first end 117 of capillary tube engaging a flow component 127 (in this case, a 90 degree angle connector), and is sealed via O-rings and positioned to align with a capillary flow passage for flow to the conditioning components downstream, in the present case, the flow would run from capillary tube to regulator inlet 6, where any entrained liquid in the flow is vaporized by a heated regulator or vaporizer.

The capillary tube 116, like the probe tip 2 has an ID formed to facilitate capillary tube capillary flow properties in the fluid flowing therethrough, which, in the present case, for wet gas (natural gas having entrained liquid) has been found to exist in a passage having an inner diameter of less than 1/32", although this figure could vary depending upon the surface tension of the liquids and other factors, further, the geometry of the capillary tube passage facilitate the flow of fluid therethrough at least at the velocity of the fluid stream from which the sample is taken, or at a higher velocity thereto.

In the present exemplary embodiment of the invention, the capillary tube 116 comprises Dursan 1/8" OD stainless steel tubing, which is situated inside the probe passage (and rack), and the present tubing having a 0.030" or less ID to prevent sample disassociation via capillary action (and maintaining or providing enhanced fluid velocity), the optimal diameter of which can vary depending upon the operational criteria and "wet gas" composition.

In the system of the present invention, it is imperative that no disassociation takes place in the sample fluid flow, from the moment the sampling occurs at the slotted probe tip, through the length of probe, and downstream to the conditioning component(s) analysis or collection.

The capillary tube would provide along its length a passage having capillary flow properties, which, to reiterate, for wet gas in the present context (natural gas having entrained liquid) has been found by the present inventor to comprise a passage having an inner diameter (ID) of 1/32" or less, the optimal ID depending upon the surface tension of the liquids and other factors. The capillary flow action, coupled with the higher flow velocities inherent in the present system, acts in concert to prevent disassociation of a representative sample comprising wet gas (gas with entrained liquids). A combination of phase diagram data and empirical testing could lead to a guide for the optimal capillary diameter/geometry, depending on the particular pipeline/flow property/application.

One or more capillary tubes can be provided in series to provide a capillary passage providing a higher velocity flow running from the outflow passage at the threaded end of probe to any conditioning components downstream. The passages may be connected via connectors commonly available in the marketplace. Alternatively, a single capillary tube may be provided running from the probe to the conditioning component. Another alternative, can comprise capillary tubing segments and sealed to one another in series. Still another alternative could comprise inserts of PTFE (otherwise known as TEFLON brand material) that can be pressed in series into existing passageways, which may be used to align and seal the capillary tube segments inserted therein in series, so that separate seals are unnecessary.

It is important that no disassociation takes place from the point of collection at the probe tip until it reaches the conditioning components downstream, for example, for vaporization via vaporizer or heated regulator. The insert (preferably PTFE material in the present embodiment) is manually placed into the passage or pressed manually (for example by sliding the insert into place). The capillary tube which in the present embodiment is formed of stainless steel, is then pressed into the insert. The insert and capillary are preferably also applied to the passages downstream, including any valve(s), conduits exterior the probe, and any enclosure coupling(s) leading from the probe to the conditioning component.

In the alternative to a capillary tube 116, the inner diameter (ID) of probe passage 8 itself could have an ID formed to maintain or increase flow velocity from the probe tip along its length, and accordingly have an ID equal to or less than the width of the opening forming the slot 108 in the slotted probe tip 2 or ID of the outflow passage 113 (i.e., less than 1/32"), the geometry formed to provide capillary action in the wet gas flowing therethrough to prevent disassociation thereof.

Continuing with FIGS. 8A-8D, the slotted probe tip 2 of the present invention can include on the back side 128 opposite slot opening 106 threaded apertures 129, 129', 129" formed to threadingly receive screws or other fasteners to facilitate the attachment of a cylindrical filter screen 130 (for example, 40×40 mesh, 0.010" wire), to envelope the outer diameter (OD) of the probe tip and prevent solids from entering the opening 106 to slot 108, but large enough for the velocity of the sample to keep fluids from accumulating. A bottom screen disc may also be provided at the second end 103' of slotted probe tip 2 held in place with a spiral retaining ring. Alternatively, a membrane may be utilized with, in addition to, or in place of screen 130 to envelope the probe tip to exclude undesirable contaminants from entering the probe. Another variation of this concept is discussed in detail in the third embodiment of the present invention, supra.

The system of the present invention ensures that the representative sample taken either in spot, batch or continuous fashion is not allowed to disassociate by providing the very small internal cavity forming the outflow passage, to maintain or enhance the fluid flow velocity through the system. The pipeline area is very large compared to the probe's very small interior and because of this vast difference, fluid in the outflow passage from the slotted probe tip to the probe will always be flowing at a higher velocity than the pipeline fluid.

The high gas velocity (higher than the source velocity of the pipeline) of the very small internal cavity/fluid outflow passage is formed to sweep all of the liquid particles at the same velocity as the gas particles being transported from the source to the probe. Therefore, it would remain "associated" with the gas from which it condensed, as verified from Applicant's own empirical testing. High velocity gas in the small internal diameter bore forming outflow passage engaging the relatively narrow slot of the probe will prevent any significant layer of liquid from accumulating on the surfaces. Even if an ultra-thin layer were to coat the probe's interior, the total area is anticipated to be small that the impact would be expected to be negligible.

Continuing with the figures, as shown, providing capillary flow downstream the slotted probe tip 2 can be provided by engaging capillary tube 116 thereto so that when the end of an insertion probe P (with slotted probe tip) is lowered or inserted (e.g., via the rack in the preferred embodiment) into a pipeline positioned in the medial or center-third area 21 of the pipe with the opening 106 forming the entrance of the slot 108 facing the flow stream, the fluid flows through said probe tip and said capillary tube utilizing capillary action to prevent disassociation of its composition. While the present illustration shows the sampling position of the probe such that the probe tip 2 is in the center-third area 21 for BLM compliance, it is noted that the probe tip can be positioned elsewhere as required.

A portion of the fluid stream comprising a "linear slice" of the fluid flow in the positioned portion of the pipe then passes into the opening, into and through the slot, then through the pressure of the flow stream is urged through the outflow passage, capillary tube with capillary flow on to the modular conditioning components for heating and/or collection, online analysis, monitoring, or other usage. As earlier indicated outflow passage in the preferred embodiment as well as downstream the probe tip to the conditioning components preferably has an inner diameter commensurate with the width of the slot formed in the body forming the slotted probe tip, resulting lesser area than the slot, so as to facilitate at least equal but more likely greater fluid velocity flow through said outflow passage, to keep the fluid from slowing and possibly disassociating.

Along with the higher velocity sweeping the wet gas sample so that it does not disassociate, conventional science recognizes that, as the inside diameter or cross sectional area of a slot or passage decreases, a static liquid having sufficient surface tension will interact with the walls of sufficiently small slot or passage to trigger static capillary functionality, a phenomenon known to occur when the static liquids adhesion to the walls is stronger than the cohesive forces between the liquid's molecules. Such a phenomenon, in combination with the higher velocity sweep, is believed to be an inherently motivating feature in the present invention when wet natural gas passes through the slot or wall when the clearance is at most (depending on various factor) equal or preferably generally less than 1/32", although the exact threshold where static capillary function can and will occur in this dynamic sweeping combination can vary depending on the composition of the wet gas, as well as other factors.

In the preferred embodiment of the present invention, the sample, once taken, is then directed to a heated conditioning component(s) to vaporize any liquids, providing a single phase sample, then to a process analyzer, monitor, sample container, or other end use.

Considering the above and foregoing, a method of sampling a wet gas from a fluid stream the present invention could therefore comprise the steps of, for example:

a. providing a probe having a probe passage formed along its length having an inner diameter having a geometry to facilitate capillary action in wet gas flowing therethrough, at a higher velocity than said fluid stream;

b. allowing wet gas to flow from said fluid stream into and through said probe so as to provide capillary action at the higher velocity;

c. allowing said capillary action to prevent disassociation of said composition of said wet gas as it flows through said probe passage.

Still further, the method of sampling a wet gas comprising gas with entrained liquid in a fluid stream of the present invention could comprise, for example, comprising the steps of:

a) providing a probe tip 2 engaging probe P, said probe tip comprising an elongated slot situated along its length;

b) laterally positioning said probe tip in the fluid stream so that said slot faces the stream;

c) utilizing said slot to receive a linear sample of flow of said stream into said body, providing received flow;

d) flowing said received flow through a passage sized to have capillary flow properties to prevent disassociation; and e) vaporizing said received flow to provide a representative sample.

As discussed, to be compliant with present BLM regulations, preferably the probe tip 2 would be situated in the center third (medial area) of the flow.

Still another embodiment of the present invention as described above may be summarized in the form of a method of sampling a wet gas from a fluid stream in the present invention could therefore comprise the steps of, for example:

a. providing a probe having a probe passage formed along its length flowing to an outflow passage having inner diameter;

b. providing capillary tubing formed to slidingly engage said inner diameter of said probe passage, said capillary tubing having formed therein a capillary passage formed to facilitate capillary motion in wet gas flowing therethrough, at a higher velocity than the fluid stream from which the sample is taken;

c. inserting said capillary tubing to engage said into said probe outflow passage;

d. allowing wet gas to flow from said fluid stream, through said probe tip into and through said capillary passage so as to provide capillary action at an equal or higher velocity than the fluid entering the probe;

e. utilizing said capillary action with equal or higher velocity flow to prevent disassociation of said composition of said wet gas as it flows through said capillary passage.

Further, the above and foregoing contemplates the method of converting a probe having a probe passage formed along its length which could comprise the steps of, for example:

a. providing a capillary adapter (in the form of an insert formed to receive a capillary tube), the capillary adapter having an outer diameter formed to slidingly engage said inner diameter of a passage, said capillary adapter having formed therein a capillary passage formed to facilitate capillary motion in wet gas flowing therethrough, at a higher velocity than the flow from which the sample is taken;

While less than 1/32" is indicated as an example of the diameter for capillary flow in the present wet gas application, it is reiterated that the optimal specific geometry can vary depending on a number of criteria. A combination of phase diagram data and empirical testing could be used as a guide to determine the optimum capillary diameter/geometry for the particular wet gas composition, taking further into account the particular pipeline/flow, property/application/environmental and other factors.

Third Embodiment of the Invention—Slotted Probe Tip with Mountable Membrane Sleeve The third embodiment of the present invention is shown in FIGS. 11A-13B, contemplating a slotted probe tip 140 comprising a body 141 having an outer wall 144 forming an diameter (OD) 144', said body 141 having a length 142, said body having mountable thereto a membrane sleeve 160 formed to slidingly envelope the length of the probe tip, providing an effective means to exclude solids as well as liquid contaminants (as desired, depending on the membrane selected) from entering the collection port (the slot) formed in the probe, as will be further discussed herein.

The exemplary embodiment of the slotted probe tip of the FIGS. 11A-11E illustrates a body 141 having slot 149 and outflow passage 150, preferably (but not exclusively) shown in the present exemplary embodiment has having capillary flow properties as described in the second embodiment of the invention discussed supra, and has an outflow extension 153 emanating from the body 141, the outflow extension 153 having receiver 152 formed therein, the outflow extension 153 preferably (but not exclusively) being threaded 154 so as to be mounted to or engage the insertion probe, said receiver 152 formed to receive 156 the end 155' capillary tube 155 (116 in FIG. 10E) to provide capillary flow from the outflow passage 150 through the length of the insertion probe to the modular conditioning or other components, apparatus, or collection vessel(s) downstream. The receiver has formed therein, about the outflow passage, an O-ring retainer 157 therein for receiving an O-ring to provide a seal about the OD 155" of the inserted end 155' of the capillary tube 155 and the ID 152' of the receiver 152, so as to provide uninterrupted capillary flow from the outflow passage 150, through the length of any insertion probe or other passage downstream the probe tip 140, to the conditioning apparatus, analyzer, or other device or collection container/means.

In the present exemplary embodiment, the capillary tube 155, like slot 149 and outflow passage 150 of the probe tip 2 has an ID or cross section formed to facilitate capillary tube capillary flow properties in the fluid flowing therethrough, which, in the present case, for the subject wet gas in the present example (natural gas having entrained liquid) has been found to exist in a passage having an inner diameter of less than 1/32", although this figure could vary depending upon the surface tension of the liquids and other factors, further, the geometry of the capillary tube passage facilitate the flow of fluid therethrough at least at the velocity of the fluid stream from which the sample is taken, or at a higher velocity thereto.

As in the second embodiment of the invention, in the present exemplary embodiment of the invention, the capillary tube 155 comprises Dursan 1/8" OD stainless steel tubing, which is situated inside the probe passage (and rack), and the present tubing having a 0.030" or less ID to prevent sample disassociation via capillary action (and maintaining or providing enhanced fluid velocity), the optimal diameter of which can vary depending upon the operational criteria and "wet gas" composition.

In the system of the present invention, it is imperative that no disassociation takes place in the sample fluid flow, from the moment the sampling occurs at the slotted probe tip, through the length of probe P (in the preferred embodiment, via capillary tube 116), to regulator inlet 6 (FIG. 3) (where the sample is conditioned via heated regulator and vaporized).

In the alternative to a capillary tube, the outflow flow 150 passage (having a an ID or cross section to facilitate capillary motion per the above discussion could extend through the receiver area to engage a coupling or exterior capillary passage having an ID formed to maintain or increase flow velocity from the probe tip along its length, and have an ID equal to or less than the cross sectional area of the slot 149 collection passage formed in the slotted probe tip 140 body 141, which passage engages the outflow passage 150 (i.e., less than 1/32"), with the cross sectional area or ID of all passages downstream the slot formed to provide capillary action in the wet gas flowing therethrough, to prevent disassociation thereof.

Although the present embodiment of the invention illustrates the probe tip configured for capillary flow, this is for exemplary purposes only and is not intended to be limiting, and the membrane sleeve feature of the present invention may be utilized in other embodiments of the probe without capillary flow properties, and is readily useable with the slot and passage configurations as revealed in the first embodiment of the present invention, supra.

As discussed in the first embodiment of the present invention, in the present embodiment, the body 141 forming the probe tip has a first 143 and second 143' ends defining a length 142 therebetween, with a slot 149 defining a narrow opening to a centrally disposed outflow passage 150 engaging said slot, said outflow passage 150 of preferably equal or less internal diameter than the slot width, said outflow passage preferably of equal or less cross-sectional area than the slot area, thus providing the "integral slice" (in the present example, less than 1/32" wide slot from the outer surface of the probe) to intersect the small ID outflow passage (less than 1/32"), so that process fluid having sample gas (which may contain entrained liquid therein) passes into the slot then is urged to flow 165 through the slot then to and through the outflow passage to the probe at an equal or higher velocity (i.e., at least the velocity of the fluid entering the slot), so as to preserve the composition of the fluid stream to that as it existed at the opening 149' of the slot and prevent disassociation or degradation of same as it flows through the slot, outflow passage, and any downstream passages to the desired destination, whether it be modular conditioning component (i.e., vaporizer, heated regulator, etc), analyzer or other device, container or other component. Continuing with the Figures, as discussed in the present application supra, the second embodiment of the invention (above) discussed the option of providing a cylindrical filter screen (130 FIGS. 8A-8D) having an ID and length formed to be mounted about and envelope the length of the body of the probe so as to cover the slotted opening, and thereby prevent the passage of solids into the slotted probe opening from the fluid stream.

Continuing with FIGS. 11A-14B, the third embodiment of the present invention provides a variation of the screen filter concept of the second embodiment, providing a cylindrical membrane 160 having a length 161 (preferably a length 142 from the second 143' end of body 141 to flange 156), a thickness 161' and an ID 162, the length 161 formed to telescopingly slide over 163 and thereby envelope the body 141 of the probe so as to envelope 159 and thereby cover the slotted opening 149, providing selective barrier (depending on the membrane used) between the slotted opening 149 and the fluid stream in which the probe is inserted or immersed, and thereby utilize the membrane to block/contain various contaminants which can include not only solids, but also liquid contaminants of various viscosities and compositions, blocking same from passing therethrough and entering the slotted probe opening 149', which contaminants might exist in the fluid stream and otherwise would enter the probe. While blocking the desired contaminants, the membrane 160 could (again, depending on the membrane selected) allow the passage of gas and even entrained liquid hydrocarbons or the like, if desired.

As shown, in the preferred present embodiment, the membrane sleeve 160 is slid 163 over the OD of the body 141 of the probe tip 140, covering the slot opening 149' in body 141, the sleeve 160 having a length 161 to envelope/cover the probe from the second end 143' of the body to about the flange 156 at the base of the threaded 154 connection of outflow extension 153.

Figures 12A, 12B:
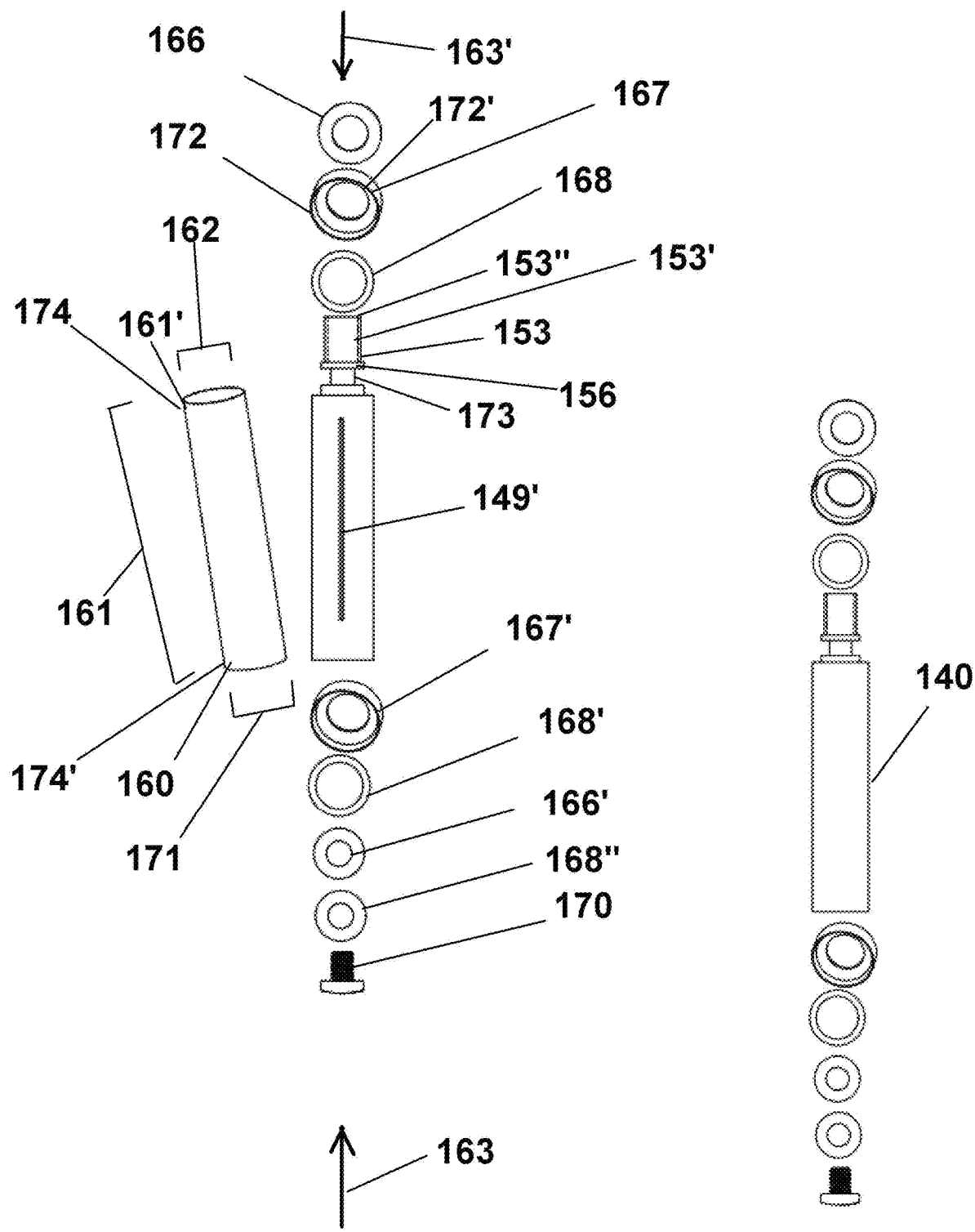
FIG. 12A is a frontal, exploded view of the third embodiment of the present invention, illustrating the slotted probe tip of FIGS. 11A-E, as well as a membrane sleeve formed to slidingly envelope outer diameter of the length of the body of the probe, along with first and second end caps and mounting hardware for securely and sealingly fastening said sleeve about said body of said probe tip, providing a means of excluding the flow of solid and liquid contaminants (the scope of which can vary depending on the membrane selected) to the slotted opening of the probe tip.
FIG. 12B is a rear view of the invention of FIG. 12A, illustrating the slotted probe tip with mounting hardware, but with the membrane sleeve enveloping the probe tip and thereby over the slot.

To secure the membrane in place mounting hardware is used which comprises, at the first end 173 of the membrane sleeve 160), a rubber gasket 168 slipped over the outflow extension 153 to rest inside the first 174 end of the membrane sleeve, a ferrule 167 (for example, of metal) slipped over outflow extension 153 to guide the 174 end of membrane sleeve against gasket 168, then a PTFE gasket 166 (eg TEFLON brand) positioned to rest upon ferrule 167. The ferrule 167 has a lip 172 having an OD 172' positioned to envelope the OD 171 at the first end 174 of membrane sleeve 160. An O-Ring 175 is provided at groove 173 (FIGS. 12A and 13B).

Figures 13A, 13B:
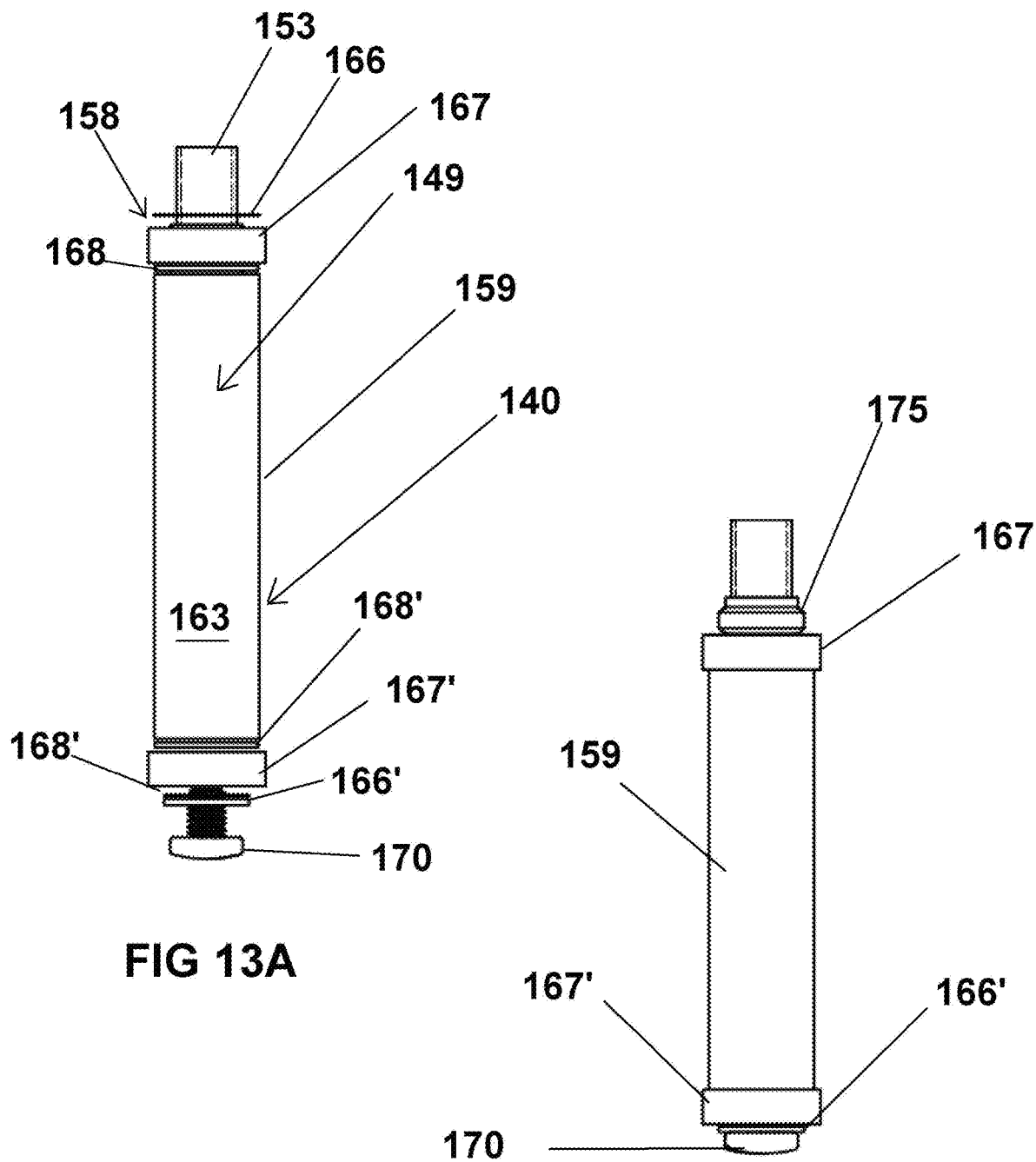
FIG. 13A is a side view of the invention of FIGS. 11A-12B, with the membrane enveloping the length of the body of the slotted probe tip, with end caps and other mounting hard ware positioned for securing same, and further illustrating a bottom threaded fastener (screw) in position for engaging the threaded aperture formed in the second end of the probe tip body.
FIG. 13B is a side view of the invention of FIG. 13A, illustrating the threaded fastener fully engaged to secure the membrane sleeve to the second end of the body, with end caps in place and a ferrule mounted to secure the membrane sleeve at the first end of the body.
Figure 14A:
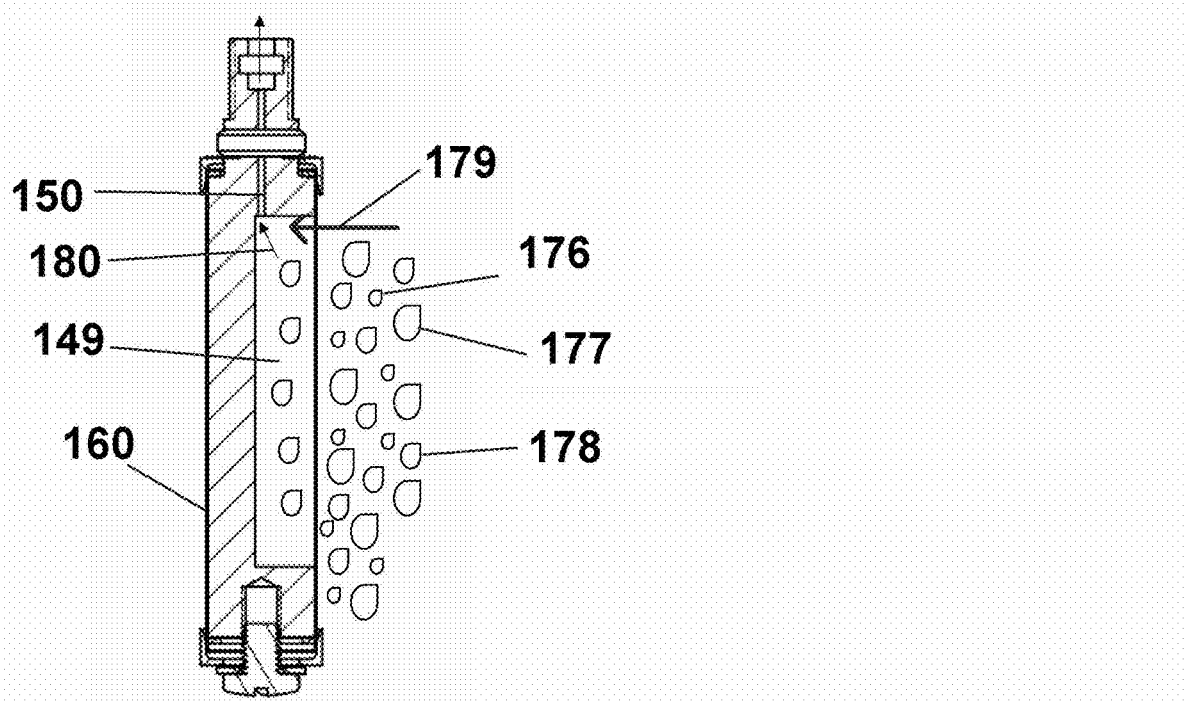
FIG. 14A is a side, cutaway view of the invention of FIG. 13B, illustrating the passage of hydrocarbon liquids through the membrane, into the elongated opening, through the slot, and to the outflow passage, the figure further illustrating the membrane blocking non-hydrocarbon contaminants and solids over 1 micron.
Figure 14B:
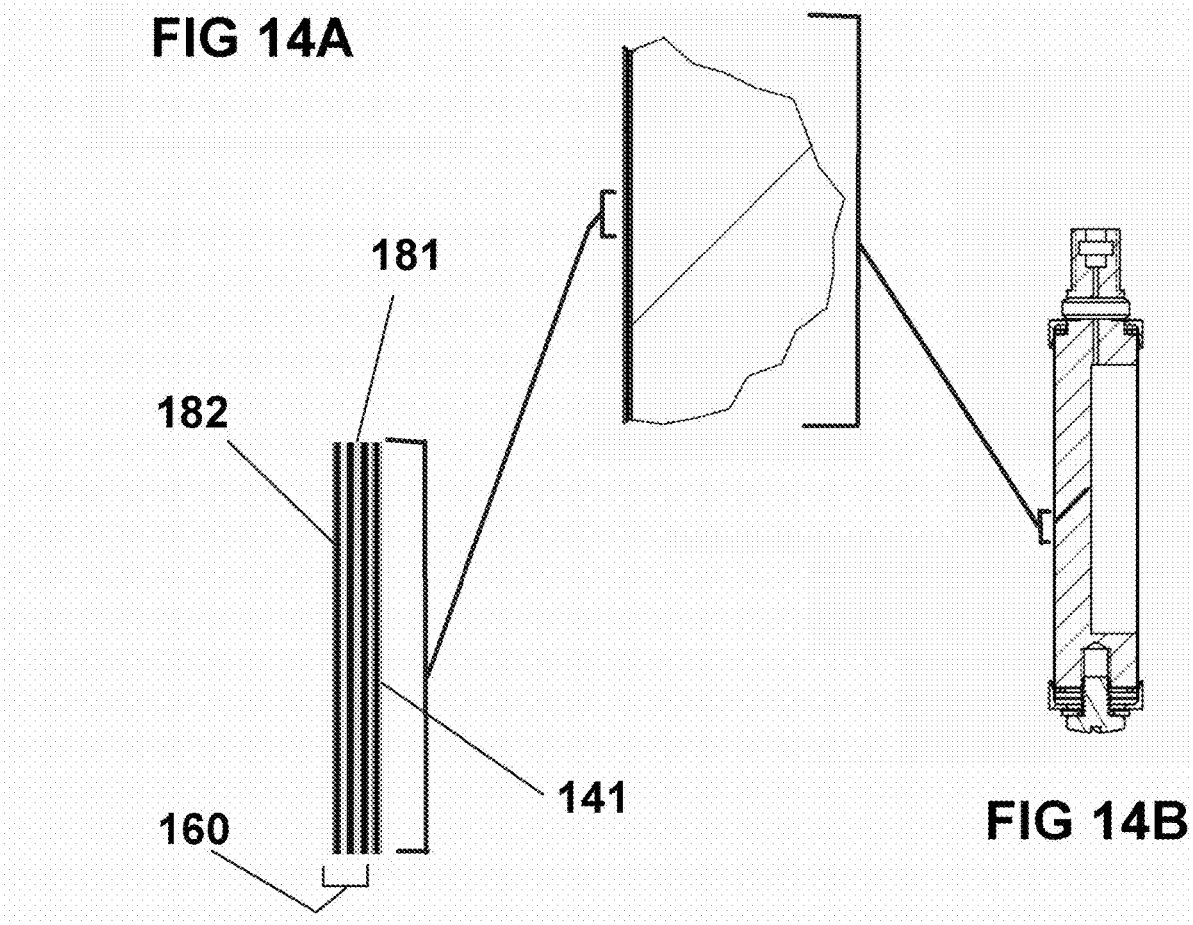
FIG. 14B is a side, cutaway view of the invention of FIG. 14A, illustrating a 10×, close-up, partially cutaway view of the membrane structure enveloping the probe body, and a further close-up, partially cutaway view of the membrane layer applied to a backing layer, which is enveloping and in contact with the body and elongated opening to the slot.

To secure the second end 174' of sleeve at the second end 143' of the probe, rubber gasket 168' is slipped into membrane sleeve 160 at the second end 174', then the second end 174' of sleeve 160 is folded over gasket 168', then ferrule 167' is slipped over the second end as shown in FIG. 13A so that it envelopes the second end 174' of membrane (which covers gasket 168'), and PTFE gasket 166' is placed over ferrule 167' with rubber gasket 168". Then screw 10 or threaded fastener is utilized to engage threaded aperture 164 in the second end 143 of body 141.

Preferably the sleeve is formed of a somewhat rigid material to hold its shape (in the present embodiment cylindrical but could vary depending on application) during installation and use, for example a backed membrane such as A+ Corporation Type 8 membrane (see Genie 225 Product Sheet, the contents of which are incorporated by reference thereto).

A membrane suitable for blocking the passage of water and other contaminants (including, for example, glycol or other additives or even solids) could comprise, for example, a GENIE brand membrane Model 225, Type 8 membrane having a pore size range of less than one micron, comprising a porous polymer membrane material with a stiff plastic mesh support composite, available from A+ Corporation of Gonzales La.

For other applications the aforementioned membrane(s) may be used, for example to block non-hydrocarbon liquids comprising polar components, immiscible in liquid hydrocarbons normally found in natural gas pipelines.

Other membranes may be utilized to block non-polar components as well, comprising for example liquid hydrocarbons normally found in natural gas pipelines.

In the present example, the membrane sleeve 160 comprises a membrane backing 181 having applied thereto a membrane 182 enveloping the probe body 141 so as to directly cover and engage the outer entrance of the elongated opening forming the slot, the membrane backing 181 used to provide structure to the membrane so that it retains its shape and resists wrinkling.

As an alternative to a membrane backing, a screen or other frame having a more flexible membrane mounted thereto is provided so that the membrane might retain its shape in operation. The aforementioned Type 8 membrane is actually a composite of PTFE membrane 182 with a polyethylene or polypropylene mesh forming the membrane backing 181 adhered to it. Again, alternatively, a PTFE membrane may be provided without the mesh and mounted directly to the screen.

Empirical testing has found that, in two phase wet gas sampling, all hydrocarbon liquids (non-polar straight chain molecules) can flow through the right membrane (for example, the Type 8 membrane) but not glycol and other polar contaminants. In addition, solid contaminants over a predetermined particle size (1 micron) would be blocked in a more efficient fashion that as screen (second embodiment of the present invention) has been shown to occur, depending on the operating environment.

Genie brand Type 6 membrane (provided by A+ Corp of Gonzales La., a related company to Applicant) is utilized to reject all liquids (polar and non-polar) See for example U.S. Pat. No. 6,357,304 B1 (Col 8 line 44). Such use could be restricted in certain designated BLM areas which provide restrictions on the use of liquid filtration in in situ analytical sampling applications, under the new BLM rules. However, it is believed that a membrane that would allow hydrocarbon liquids to pass through, while blocking non-hydrocarbon contaminants (such as glycol) could be useful under these applications, such as by using, for example, the Type 8 membrane used currently in Genie model 225 see Product Sheet.

Unlike the screen disclosed in the second embodiment of the present invention, the use of such a membrane before the probe opening could result in a loss of velocity of the fluid stream as it passes through the membrane. Nonetheless, even with a reduction in flow velocity, the probe having capillary passages (as discussed in the second and third embodiments of the present invention) would utilize capillary action via the fluid flowing through the capillary passages to maintain the compositional characteristics for the fluid composition flowing into and through the probe, even with reduced flow velocity due to passage through the aforementioned membrane.

Further, a probe without capillary flow characteristics, but with fluid passages configured to provide flow from the slotted probe opening through the outflow passage and downstream to the conditioning component, analyzer or the like so as to maintain flow velocity through and downstream the probe without reduction in flow velocity (which can be achieved if there is no reduction of cross-sectional area of the flow passages downstream the slotted probe opening), could also be used to ensure such compositional characteristics of the fluid flow would be likewise maintained.

With the membrane sleeve of the present invention, the user can select the degree or characteristics of separation, by changing the membrane, as there are many options commercially available. For example, a user may utilize a Type 6 membrane (phase separating material capable of separating gas and liquid phases available through A+ Corporation of Gonzales, La. USA) to reject all liquids and thereby allow only sample gas to enter the probe. Or Type 8 membrane (phase separating material capable of separating two immiscible liquid phases) to reject only polar contaminates like water and glycols, etc. Other filter materials may comprise filter paper, paper leaf, ". . . a sheet of phase-separating material . . . may be a membrane capable of separating two immiscible phases . . . " as well as ". . . a membrane capable of separating gas and liquid phases . . . " See U.S. Pat. No. 7,444,954, Col 5, lines 13-23, the contents of which are incorporated herein by reference thereto. Note U.S. Pat. No. 7,444,954 is a CIP of U.S. Pat. No. 7,097,693 which lists as one of the inventors the same inventor in the present application. Both of these sheet type phase separating materials also filter out solid particles over 1 micron in size. An example of a company providing such phase separating membranes, for example, is SKC, ltd. in Dorset, UK, having a homepage at www.skcltd.com.

For transmission quality gas pipelines where only single-phase sample is obtained via, for example, the Type 6 membrane or the like could be used which allows only the passage of gas therethrough. With only gas flowing through the probe, neither the velocity advantage nor the capillary advantage available in the present system would be needed. Nonetheless, the present slotted probe would still be useful as it can be configured to sample only the center-third of the fluid stream, as discussed in the second embodiment supra, as opposed to conventional sampling probes with an inlet hole at the end of the tip such as with a tube or pipe opening (which would provide a more limited sample of the overall fluid stream). This is because the slotted probe of the present invention is oriented to face the gas flow with a length corresponding to the desired sample area, i.e., the center third of the ID of the pipeline versus the conventional opening on the bottom of a probe, tube, or pipe as taught in Applicants direct drive probes, for example, as enumerated in U.S. Pat. No. 8,522,530 (FIG. 4).

ELEMENTS OF THE INVENTION

H Heated Zone
F, F' fluid stream Flow
L pipeline
P, P' insertion probe
C collection apparatus
S Slot
1 gas with entrained liquids
2 slotted probe tip
3 probe isolation valve
4 substrate coupling
5 modular sample conditioning system
6 regulator inlet
9 regulator
20 probe passage
21 medial area of pipe/stream
22 regulator threaded fasteners
24 OD of probe
25, length, rack'
31 body
32 length
33, 33' first upper, second lower ends
34, 34' outer wall, outer diameter
35 longitudinal axis
36 elongated opening (continuous)
37, 37' length, width
38' depth
38 slot
39 central axis
40, 40' first and second ends and
41, 41' first and second side walls having
42, 42' outer, inner edge
43 outflow passage
43' ID pipe
44' outflow passage ends
45 outflow passage diameter
46 lowered
48 slotted probe tip
16 lowered
101 body
102,' insertion probe first, second ends
103,' first, second ends of body 101
104 outer wall
105 longitudinal axis
106 opening
107,' length, width
108 slot
109 O-Ring saddle (probe tip)
110 opening 106 ends
111,' first, second side walls
112,' outer, inner edges
113 outflow passage
114 threaded end of probe
115 ID outflow passage
116 capillary tube
117,' first, second ends
119 O-Ring retainer
120 receiver
121,' O-Ring,"
122 Probe lower end O-ring seal
127 flow component
128 back side of probe opposite slot opening
129,',"threaded apertures
130 solids filter screen
140 slotted probe tip
141 body
142 length
143,' first upper, second lower ends
144,' outer wall, OD
145 longitudinal axis 146,' slot/elongated, continuous
147,' length/width
148 depth
149,' slot, opening
150 outflow passage
152,', "receiver, ID
153,', "outflow extension
154 threaded
155,', "capillary tube, end, OD
156,' inserted, ID
157 o-ring retainer
158 flange
159 envelope
160 membrane sleeve
161,' length, thickness
162 ID
163,' slide over, mounted
164 threaded aperture
165 fluid flow
166,' teflon gasket
167,' metal ferrule
168,','rubber gasket
169,' metal ferrule
170 screw
171 OD
172 Lip, OD
173 O-Ring Groove
174,' first, second ends
175 O-Ring
176 solid contaminants over 1 micron
177 liquid contaminants
178 liquid hydrocarbons
179 passes through membrane
180 flows to outlet passage 150
181 membrane backing
182 membrane The invention embodiments herein described are done so in detail for exemplary purposes only, and may be subject to many different variations in design, structure, application and operation methodology. Thus, the detailed disclosures therein should be interpreted in an illustrative, exemplary manner, and not in a limited sense.

I claim:

1. A device for sampling a wet gas for compositional analysis having a composition in a fluid stream, comprising:
   a probe tip having a length, and an outlet passage having an inner diameter less than 1/32";
   said probe tip having an elongated opening less than 1/32" wide formed along its length, said elongated opening leading to said outlet passage;
   said elongated opening and outlet passage in said probe tip formed to facilitate capillary action in wet gas flowing therethrough at least at the velocity of said fluid flowing into said probe tip;
   whereby wet gas flows into said elongated opening and through said outlet passage without disassociation of said composition of said wet gas.

2. The device of claim 1, wherein said device further comprises a membrane upstream said fluid passage formed to block contaminants, while allowing hydrocarbon fluids to pass through.

3. The device of claim 2, wherein said membrane comprises a tubular sleeve enveloping said probe tip.

4. A device for sampling a wet gas for compositional analysis having a composition in a fluid stream, comprising:
   a probe tip having a length, and an outlet passage having an inner diameter;
   said probe tip having an elongated opening formed along its length, said elongated opening leading to said outlet passage;
   said elongated opening and outlet passage in said probe tip formed to facilitate the flow of wet gas therethrough at least at the velocity of said fluid flowing into said probe tip, while preventing disassociation of said composition of said wet gas flowing therethrough; and
   a membrane comprising a tubular sleeve enveloping said probe tip upstream said fluid passage, said membrane formed to block contaminants, while allowing hydrocarbon fluids to pass through.

5. The device of claim 4, wherein said elongated opening of said probe tip comprises a slot having an opening less than 1/32" wide, and said outlet passage of said probe tip having an inner diameter less than 1/32", said slot and outlet passage of said probe tip formed to facilitate capillary action in wet gas flowing therethrough.

* * * * *

UNITED STATES PATENT AND TRADEMARK OFFICE
CERTIFICATE OF CORRECTION

| | |
|---|---|
| PATENT NO. | : 10,866,167 B1 |
| APPLICATION NO. | : 15/977441 |
| DATED | : December 15, 2020 |
| INVENTOR(S) | : Valmond Joseph St Amant, III |

It is certified that error appears in the above-identified patent and that said Letters Patent is hereby corrected as shown below:

On the Title Page

Item (73) Assignee, replace "Maveaux Holdina" with -- Mayeaux Holding --

Signed and Sealed this
Twenty-fifth Day of October, 2022

Katherine Kelly Vidal
*Director of the United States Patent and Trademark Office*